United States Patent
Mourad et al.

(10) Patent No.: US 7,296,318 B2
(45) Date of Patent: Nov. 20, 2007

(54) TOOTHBRUSH EMPLOYING AN ACOUSTIC WAVEGUIDE

(75) Inventors: Pierre D. Mourad, Seattle, WA (US); Francis G. Olson, Seattle, WA (US); Roger Lee Thompson, Kirkland, WA (US); Jason L. Seawall, Seattle, WA (US)

(73) Assignee: University of Washington, Seattle, WA (US)

( * ) Notice: Subject to any disclaimer, the term of this patent is extended or adjusted under 35 U.S.C. 154(b) by 438 days.

(21) Appl. No.: 10/981,735

(22) Filed: Nov. 3, 2004

(65) Prior Publication Data

US 2005/0091770 A1 May 5, 2005

Related U.S. Application Data

(60) Provisional application No. 60/517,638, filed on Nov. 4, 2003.

(51) Int. Cl.
*A61C 17/22* (2006.01)
(52) U.S. Cl. ............... 15/22.1; 433/119; 601/142
(58) Field of Classification Search ............ 15/22.1, 15/110; 433/118, 119; 601/142
See application file for complete search history.

(56) References Cited

U.S. PATENT DOCUMENTS

| RE2,875 E | 2/1868 | Ames et al. |
|---|---|---|
| 3,196,299 A | 7/1965 | Kott |
| 3,335,443 A | 8/1967 | Parisi et al. |
| 3,563,233 A * | 2/1971 | Bodine ............ 601/72 |
| 3,809,977 A | 5/1974 | Balamuth et al. |
| 3,828,770 A | 8/1974 | Kuris et al. |
| 3,840,932 A | 10/1974 | Balamuth et al. |

(Continued)

FOREIGN PATENT DOCUMENTS

| JP | 10165228 A | 6/1998 |
|---|---|---|
| JP | 2004148079 A | 5/2004 |
| SU | 506421 A1 | 3/1978 |
| WO | 9213498 A1 | 8/1992 |
| WO | 9415546 A1 | 7/1994 |

OTHER PUBLICATIONS

Apfel, R.E., and C.K. Holland, "Gauging the Likelihood of Cavitation from Short-Pulse, Low-Duty Cycle Diagnostic Ultrasound," *Ultrasound in Medicine and Biology* 17(2):179-185 (1991).

(Continued)

*Primary Examiner*—Mark Spisich
(74) *Attorney, Agent, or Firm*—Christensen O'Connor Johnson Kindness PLLC

(57) ABSTRACT

A power toothbrush (10) is disclosed having a handle (15) containing a rechargeable battery (12), an ultrasonic drive circuit (14), a sonic component (16) such as a motor, and a control unit (18). The handle is connected to a toothbrush head (20) preferably having a plurality of bristles (26) and an ultrasonic transducer (22) that is operatively connected to a waveguide (24) that extends from the toothbrush head generally adjacent the bristles. The waveguide facilitates the transmission of acoustic energy into the dental fluid. It is contemplated that the waveguide may be utilized in manual or power toothbrushes, and in a combination without the sonic component, or in a combination without the ultrasonic transducer. Toothbrushes disclosed herein achieve improved plaque and stain removal from the teeth as well as interproximal and subgingival regions, while enhancing the user experience, massaging the gums, and stimulating dental tissue.

99 Claims, 16 Drawing Sheets

U.S. PATENT DOCUMENTS

| | | |
|---|---|---|
| 3,941,424 A | 3/1976 | Balamuth et al. |
| 3,980,906 A | 9/1976 | Kuris et al. |
| 4,071,956 A | 2/1978 | Andress |
| 4,192,035 A | 3/1980 | Kuris |
| 4,333,197 A | 6/1982 | Kuris |
| 4,731,019 A | 3/1988 | Martin |
| 4,991,249 A | 2/1991 | Suroff |
| 5,138,733 A | 8/1992 | Bock |
| 5,150,492 A | 9/1992 | Suroff |
| 5,247,716 A | 9/1993 | Bock |
| 5,311,632 A | 5/1994 | Center |
| 5,343,883 A | 9/1994 | Murayama |
| 5,369,831 A | 12/1994 | Bock |
| 5,378,153 A | 1/1995 | Giuliani et al. |
| 5,546,624 A | 8/1996 | Bock |
| RE35,712 E | 1/1998 | Murayama |
| 5,938,612 A | 8/1999 | Kline-Schoder et al. |
| 5,987,681 A | 11/1999 | Hahn et al. |
| RE36,669 E | 4/2000 | Zilincar, III |
| 6,190,167 B1 | 2/2001 | Sharp |
| 6,203,320 B1 | 3/2001 | Williams et al. |
| 6,421,865 B1 | 7/2002 | McDougall |
| 6,421,866 B1 | 7/2002 | McDougall |
| 6,446,295 B1 | 9/2002 | Calabrese |
| 6,500,121 B1 | 12/2002 | Slayton et al. |
| 6,513,182 B1 | 2/2003 | Calabrese et al. |
| 6,619,957 B1 | 9/2003 | Mosch et al. |
| 2002/0095734 A1 | 7/2002 | Wong |
| 2002/0116775 A1 | 8/2002 | Wong |
| 2002/0124333 A1 | 9/2002 | Hafliger et al. |
| 2003/0060736 A1 | 3/2003 | Martin et al. |
| 2003/0079304 A1 | 5/2003 | Dworzan |
| 2003/0079305 A1 | 5/2003 | Takahata et al. |

OTHER PUBLICATIONS

Chang, P.P., et al., "Thresholds for Inertial Cavitation in Albunex Suspensions Under Pulsed Ultrasound Conditions," *IEEE Transactions on Ultrasonics, Ferroelectrics, and Frequency Control* 48(1):161-170, Jan. 2001.

Holland, C.K., and R.E. Apfel, "An Improved Theory for the Prediction of Microcavitation Thresholds," *IEEE Transactions on Ultrasonics, Ferroelectrics, and Frequency Control* 36(2):204-208, Mar. 1989.

Krasovitski, B., and E. Kimmel, "Shear Stress Induced by a Gas Bubble Pulsating in an Ultrasonic Field Near a Wall," *IEEE Transactions on Ultrasonics, Ferroelectrics, and Frequency Control* 51(8):973-979, Aug. 2004.

Leighton, T.G., "Bubble Population Phenomena in Acoustic Cavitation," *Ultrasonics Sonochemistry* 2(2):S123-S136, 1995.

Mesiwala, A.H., et al., "High-Intensity Focused Ultrasound Selectively Disrupts the Blood-Brain Barrier in Vivo," *Ultrasound in Medicine and Biology* 28(3):389-400, Mar. 2002.

Poliachik, S.L., et al., "Activation, Aggregation and Adhesion of Platelets Exposed to High-Intensity Focused Ultrasound," *Ultrasoound in Medicine and Biology* 27(11):1567-1576, 2001.

Rooney, J.A., "Hemolysis Near an Ultrasonically Pulsating Gas Bubble," *Science* 169(948):869-871, Aug. 28, 1970.

Roy, R.A., et al., "An Acoustic Backscattering Technique for the Detection of Transient Cavitation Produced by Microsecond Pulses of Ultrasound," *Journal of Acoustics Society of America* 87(6):2451-2458, Jun. 1990.

Singer, C.A., et al., "The Mitogen-Activated Protein Kinase Pathway Mediates Estrogen Neuroprotection After Glutamate Toxicity in Primary Cortical Neurons," *Journal of Neuroscience* 19(7):2455-2463, Apr. 1, 1999.

Stoodley, P. et al., "Biofilm Material Properties as Related to Shear-Induced Deformation and Detachment Phenomena," *Journal of Industrial Microbiology & Biotechnology* 29(6):361-367, Dec. 2002.

Zauhar, G. et al., "Studies of Acoustic Streaming in Biological Fluids with an Ultrasound Doppler Technique," *British Journal of Radiology* 71(843):297-302, Mar. 1998.

* cited by examiner

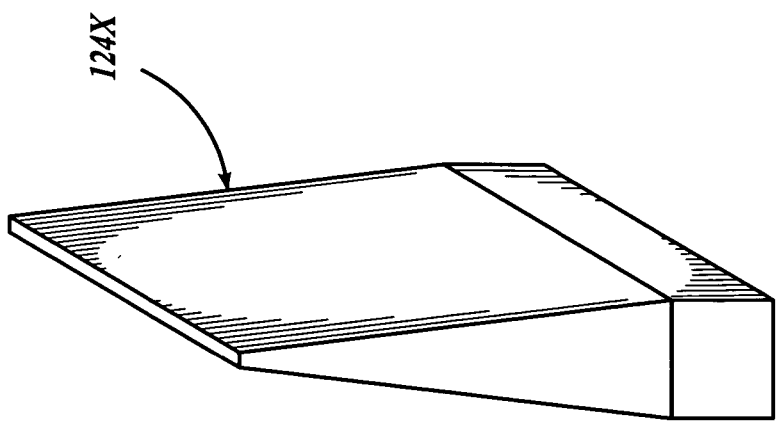
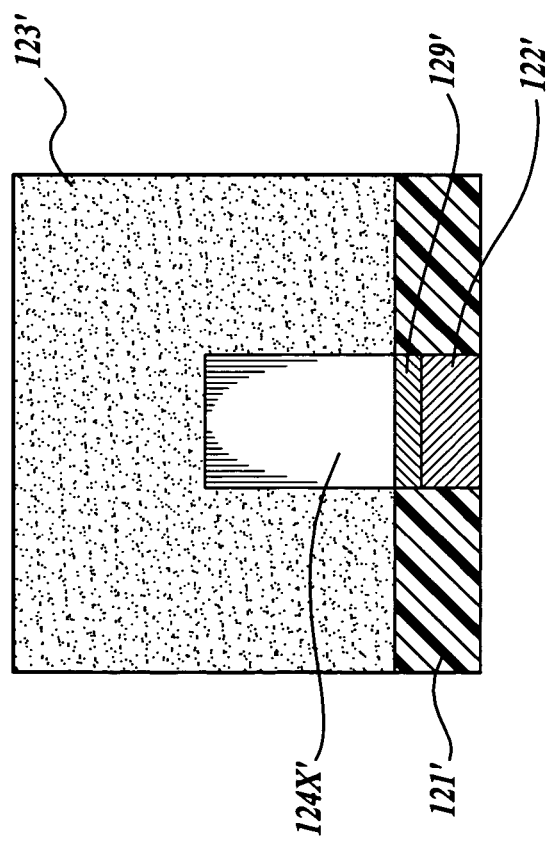
Fig.3B.
Fig.3A.

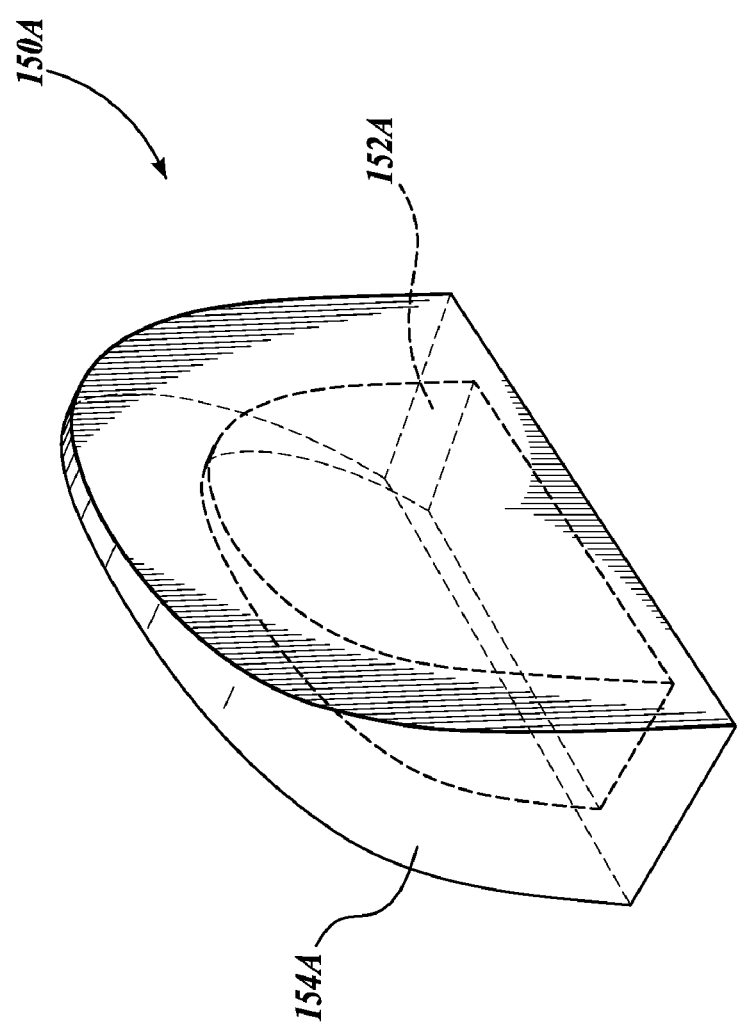

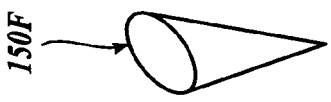
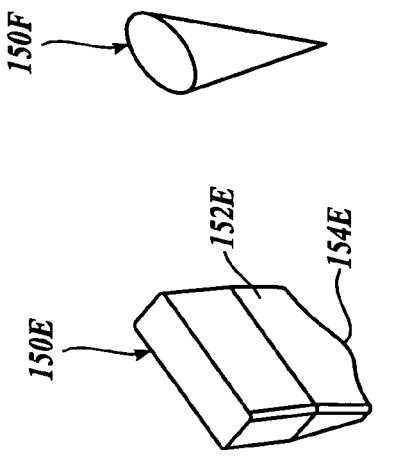
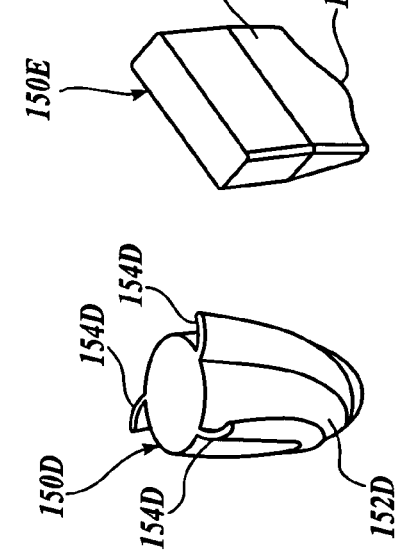
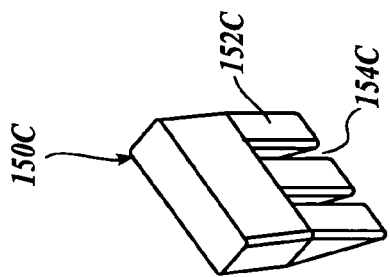
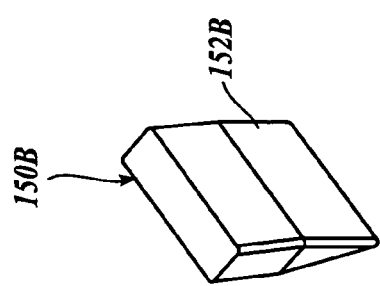
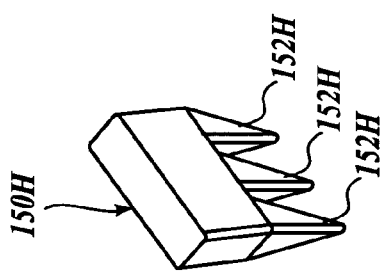
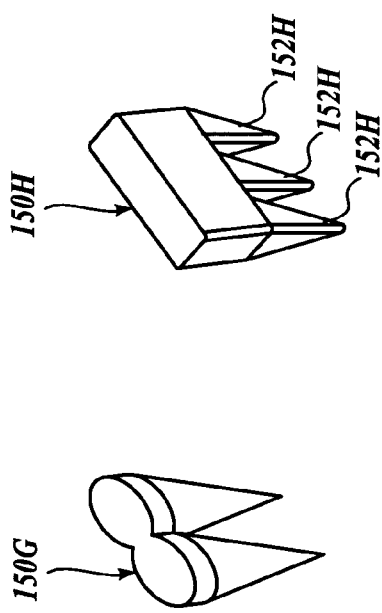

TOOTHBRUSH EMPLOYING AN ACOUSTIC WAVEGUIDE

CROSS-REFERENCE TO RELATED APPLICATION

This application claims the benefit of U.S. Provisional Patent Application No. 60/517,638, filed on Nov. 4, 2003, the disclosure of which is hereby expressly incorporated by reference, and priority from the filing date of which is hereby claimed under 35 U.S.C. § 119.

FIELD OF THE INVENTION

The present invention relates generally to the fields of toothbrushes and, more specifically, to toothbrushes that employ acoustic mechanisms. BACKGROUND OF THE INVENTION Existing power toothbrushes, even the most effective, leave clinically significant plaque at tooth-contact surfaces, at the gingival-tooth contact points, below the gingiva and beyond the direct reach of the bristles or other toothbrush components. Previous attempts at creating ultrasonic toothbrushes failed to exploit microbubble formation in dental fluid for purposes of facilitating plaque removal, or failed to consider microbubbles and macrobubbles as a potential impediment to ultrasound propagation beyond the bristle tips. Some early toothbrushes that employed ultrasound technology attempted propagation of ultrasound waves from the base of the bristles either through the bristles themselves or through the bubbly dental fluid that fills the spaces between the bristles. See, e.g., U.S. Pat. No. 5,138,733, No. 5,247,716, No. 5,369,831, and No. 5,546,624 to Bock. Because conventional toothbrush bristles and bubbly dental fluid can reduce rather than facilitate the propagation of ultrasound waves, those toothbrushes fell short of achieving efficient ultrasound wave propagation. Also, the ultrasound systems in prior art toothbrushes did not take advantage of the specific bubbly structure within dental fluid.

Synopsis of the Art

U.S. Pat. No. 3,335,443 to Parisi discloses a brush that is coupled to an ultrasonic, vibratory handheld dental instrument that is capable of being vibrated at high sonic and ultrasonic frequencies.

U.S. Pat. No. 3,809,977 to Balamuth et al., which reissued as U.S. Pat. No. RE 28,752, discloses ultrasonic kits, ultrasonic motor constructions, and ultrasonic converter designs for use alone or in combination. The ultrasonic motor may be of piezoelectric material having a removable tip and is contained in a housing having an electrical contact means adapted to be plugged into an adapter that is connected to a converter.

U.S. Pat. No. 3,828,770 to Kuris et al. discloses a method for cleaning teeth employing bursts of ultrasonic mechanical vibration at an applicator repeated at a sonic frequency to produce both ultrasonic and sonic vibratory motion during use.

U.S. Pat. No. 3,840,932 and No. 3,941,424 to Balamuth et al. disclose an ultrasonic toothbrush applicator in a configuration to be ultrasonically vibrated to transmit mechanical vibrations from one end to a bristle element positioned at the other end.

U.S. Pat. No. 4,071,956 to Andress discloses a device that is not a toothbrush, for removing dental plaque by ultrasonic vibrations.

U.S. Pat. No. 4,192,035 to Kuris discloses an apparatus comprising an elongated member formed of a piezoelectric member with a pair of contacting surfaces with a brush member adapted to be received within the human mouth. A casing adapted into a handle is configured to receive the piezoelectric member.

U.S. Pat. No. 4,333,197 to Kuris discloses an ultrasonic toothbrush that includes an elongated handle member in the form of a hollow housing having disposed therein a low voltage coil and cooperating ferrite core that is driven at ultrasonic frequencies. A brush member is affixed to the core and is adhesively affixed to an impedance transfer device that is adhesively affixed to the core material. The impedance transfer device insures maximum transfer of ultrasonic energy from the core material to the brush.

U.S. Pat. No. 4,991,249 and No. 5,150,492 to Suroff disclose an ultrasonic toothbrush having an exchangeable toothbrush member that is removably attached to an ultrasonic power member.

U.S. Pat. No. 5,138,733 to Bock discloses an ultrasonic toothbrush having a handle, a battery pack, an electronics driving module, a piezoelectric member, and a removable brush head. The piezoelectric crystal resonates, expands and contracts volumetrically, in tune with the frequency supplied by the electronic driving modules, thereby converting electronic energy into sound-wave energy.

U.S. Pat. No. 5,247,716 to Bock discloses a removable brush head for an ultrasonic toothbrush having a plurality of bristle clusters, a substantially tubular body constructed of a flexible material, and tensioning means securing the brush head to the ultrasonic device, providing for the efficient transmission of ultrasonic frequency vibrations from the device via the brush head.

U.S. Pat. No. 5,311,632 to Center discloses a device for removing plaque from teeth comprising a toothbrush having a thick, cylindrical, hollow handle encompassing (1) an electric motor that is actuable to cause rotation of an eccentrically mounted member and vibration of the entire device, and (2) an ultrasonic transducer actuable to produce high frequency sound waves along the brush.

U.S. Pat. No. 5,369,831 to Bock discloses a removable brush head for an ultrasonic toothbrush.

U.S. Pat. No. 5,546,624 to Bock discloses an ultrasonic toothbrush including a handle constructed of a rigid material, a battery pack, an electronics driving module, a piezoelectric member, and a removable brush head. The piezoelectric crystal resonates, expands and contracts volumetrically, in tune with the frequency supplied by the electronic driving module and thereby converts the electronic energy into sound-wave energy.

U.S. Pat. No. 6,203,320 to Williams et al. discloses an electrically operated toothbrush and method for cleaning teeth. The toothbrush includes a handle, a brush head connected to the handle having a plurality of hollow filament bristles, passageways through the handle and brush head for transporting fluid into and through the hollow filament bristles, an electrical energy source in the handle, and a vibratory element for imparting a pulsation to the fluid being transported.

U.S. Patent Publication No. 2003/0079305 to Takahata et al. discloses an electric toothbrush in which a brush body is simultaneously oscillated and reciprocated. The electric toothbrush comprises a casing main body, an arm extending above the casing main body, a brush body arranged in a top end of the arm, and an ultrasonic motor arranged in a top end inside of the arm for driving the brush body.

U.S. Pat. No. RE 35,712, which is a reissue of U.S. Pat. No. 5,343,883 to Murayama, discloses an electric device (i.e., a flosser) for removal of plaque from interproximal surfaces. The device employs sonic energy and dental floss secured between two tines of a flexible fork removably attached to a powered handle. The electric motor revolves at sonic frequencies to generate sonic energy that is transmitted to the flexible fork.

U.S. Pat. No. 6,619,957 to Mosch et al. discloses an ultrasonic scaler comprising a scaler tip, actuator material, a coil, a handpiece housing, and an air-driven electrical current generator. The actuator material, coil, and air-driven electrical current generator are all encompassed within the handpiece housing.

U.S. Pat. No. 6,190,167 to Sharp discloses an ultrasonic dental scaler for use with a dental scaler insert having a resonant frequency. The dental scaler insert is removably attached to a handpiece having an energizing coil coupled to a selectively tunable oscillator circuit to generate a control signal having an oscillation frequency for vibrating the dental scaler.

U.S. Pat. No. 4,731,019 to Martin discloses a dental instrument for scaling by ultrasonic operation. The instrument of the dental instrument has a distal end with a hook-like configuration with a conical pointed end and comprising abrasive particles, typically diamond particles.

U.S. Pat. No. 5,150,492 to Suroff discloses an ultrasonic toothbrush having an exchangeable ultrasonic implement that may be removably mounted to an ultrasonic power means that is encompassed within the toothbrush handle.

U.S. Pat. No. 5,378,153 to Giuliani discloses a dental hygiene apparatus having a body portion and an extended resonator arm. The apparatus employs an electromagnet in its body that acts in combination with two permanent magnets to achieve an oscillating action about a torsion pin. The arm is driven such that the bristle-tips operate within ranges of amplitude and frequency to produce a bristle tip velocity greater than 1.5 meters per second to achieve cleansing beyond the tips of the bristles.

There remains a need in the art for toothbrush designs that achieve improved dental cleaning properties between the teeth and gums, at points of contact between the teeth, and beyond the direct action of the bristles.

SUMMARY OF THE INVENTION

The present invention fulfills these and other related needs by providing toothbrushes, including power and manual toothbrushes, that employ an acoustic waveguide, either alone or in combination, with an ultrasonic transducer and/or sonic component to achieve improved plaque and stain removal and user experience. Accordingly, within certain embodiments, the present invention provides power toothbrushes having one or more acoustic waveguide that is capable of propagating and possibly focusing acoustic waves transmitted by an ultrasonic transducer into the dental fluid, thereby inducing cavitation of microbubbles and, in addition or alternately, inducing acoustic streaming, with a consequent improvement in the loosening and removal of dental plaque from dental surfaces and interproximal regions. When used in combination with a sonic component, the acoustic waveguide can, additionally or alternatively, be made to vibrate such that the acoustic waveguide contributes to enhanced fluid flow in the oral cavity and to the formation of microbubbles in the dental fluid, beyond the reach of the acoustic waveguide and/or toothbrush head bristle tips.

When used in combination with a sonic component, the enhanced bubbly fluid flow generated by the acoustic waveguide can, additionally or alternatively, work synergistically with the ultrasound transmitted through the acoustic waveguide to further facilitate plaque and stain removal beyond the reach of the acoustic waveguide and/or toothbrush head bristle tips.

In an embodiment of the present invention, an ultrasonic transducer is utilized at the toothbrush head, at the base of and in operable proximity to an acoustic waveguide or, alternatively, mechanically coupled to the toothbrush head from within the toothbrush handle via an acoustically transmitting conduit (made of metal, gel, or fluid). In either embodiment, the ultrasonic transducer transmits ultrasonic waves to the acoustic waveguide, which, in turn, propagates those ultrasonic waves into the dental fluid such that the waves are effective in causing cavitation of microbubbles within the dental fluid and, alternatively or additionally, acoustic streaming. Within certain embodiments, toothbrushes of the present invention may also comprise one or more toothbrush bristles that contribute to the generation of microbubbles within the dental fluid. The ultrasonic waves cause cavitation of those microbubbles, which, in turn, results in the improved plaque and stain removal properties of toothbrushes disclosed herein.

Additional embodiments of the present invention provide power toothbrushes having an ultrasonic transducer and an acoustic waveguide in further combination with a sonic component that operates within the audible frequencies to mechanically move the brush head, including the bristles and acoustic waveguide, to increase flow of the dental fluid at a velocity and intensity required to contribute to microbubble production. The acoustic waveguide and ultrasonic waves that it transmits act in a synergistic fashion to produce a scrubbing bubbly jet within the dental fluid, both by increasing the instantaneous spatial distribution of bubbles available for activation, and by increasing the distribution of ultrasound owing to the sonic motion of the acoustic waveguide. The acoustic waveguide and ultrasonic waves also act synergistically to create a bubbly jet by each contributing to the acceleration of the bubbly fluid, the acoustic waveguide by pushing fluid directly and the ultrasonic waves by inducing acoustic streaming.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A is a diagram depicting a finite element model simulation geometry of a toothbrush head as shown in FIG. 2A, wherein the exemplary acoustic waveguide has a tapered profile;

FIG. 3B is a perspective view of the tapered profile waveguide shown in FIG. 3A;

FIG. 5A is a combined Doppler (inside the box) and B-mode (outside the box) image depicting fluid flow induced by an ultrasonic toothbrush without an acoustic waveguide and without bristle tip motion (bristle tips (BT) and bristle plate (BP) at the bottom of bristles);

FIG. 5B is a combined Doppler and B-mode image depicting fluid flow induced by an ultrasonic toothbrush without an acoustic waveguide but with bristle tip motion (MB) and demonstrating absence of any measurable fluid flow (FF) beyond the bristles;

FIG. 5C is a B-mode ultrasound image depicting fluid flow induced by an ultrasonic toothbrush with an acoustic waveguide, wherein the waveguide is made to vibrate by a sonic component and showing that the vibrating acoustic waveguide generated a jet of bubbly fluid moving away from the toothbrush head;

FIG. 5D is a Doppler and B-mode ultrasound image of the same ultrasonic toothbrush as described for FIG. 5C, further showing significant fluid flow (FF) and bubble (B) formation beyond the bristle tips;

FIGS. 9A-H depict geometries of various exemplary acoustic waveguides for use in the toothbrush heads of the present invention.

DETAILED DESCRIPTION OF THE PREFERRED EMBODIMENT

Figure 1:
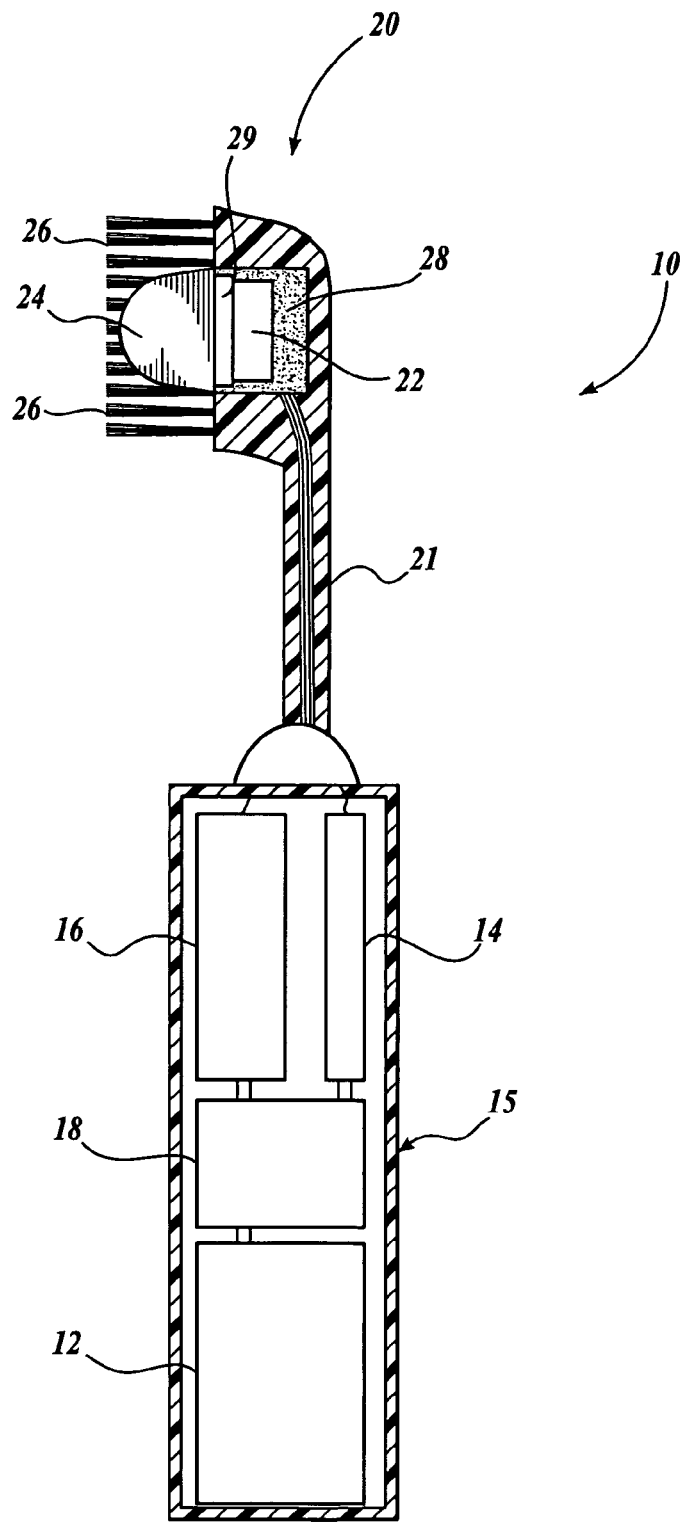
FIG. 1 is a diagram depicting an exemplary power toothbrush of the present invention.

The present invention is based upon the discovery that a toothbrush employing an acoustic waveguide, either alone or in combination with an ultrasonic transducer and/or sonic component, yields improved cleaning properties as compared to existing power toothbrush technologies. It is contemplated that toothbrushes according to the present invention may or may not include a number of conventional bristles, as discussed below. As described in detail herein, toothbrushes according to the present invention are effective in (1) increasing bubbly fluid flow by motion, including sonic motion, of the acoustic waveguide and bubble formation by the waveguide and/or one or more toothbrush bristles; (2) transmitting focused ultrasonic waves generated by an ultrasonic transducer and propagating those waves through an acoustic waveguide into the dental fluid to achieve improved plaque disruption and removal; and/or (3) facilitating bubbly fluid flow and transmitting ultrasound to interact optimally and maximally at and beyond-the-bristles (e.g., between about 0.5 mm and about 5 mm from the bristle tip, more typically between about 1 mm and about 3 mm from the bristle-tip, within the dental fluid.

Thus, within certain embodiments, the present invention provides toothbrushes, including manual toothbrushes and power toothbrushes, comprising an acoustic waveguide. In certain embodiments of the present invention, toothbrushes are provided that comprise an acoustic waveguide in combination with an ultrasonic transducer, which, together act upon the microscopic bubbly flow within the dental fluid, either as a consequence of brushing with a bristled toothbrush head and/or the motion of the acoustic waveguide acted upon by the sonic component, to induce cavitation, microstreaming, and acoustic streaming within the dental fluid. Therefore, yet additional embodiments of the present invention provide toothbrushes comprising an acoustic waveguide in combination with an ultrasonic component and in further combination with a sonic component. The sonic component, in combination with an acoustic waveguide, being fabricated of a suitable material, and/or in combination with one or more toothbrush bristles, is further responsible for generating a favorable mouth feel, stimulating and messaging the gums and other dental tissue, that in turn, promote an improved dental cleaning experience.

All U.S. and foreign patents and patent applications and all other references, whether cited supra or infra, are hereby incorporated by reference in their entireties.

Definitions and Parameters Governing the Operation of Inventive Toothbrush Technologies As used herein, the terms "ultrasound" or "ultrasonic" refer to sound of a frequency higher than, and outside of, the audible range of the human ear—generally higher than approximately 20 kHz. Typically, ultrasonic transducers employed in the toothbrushes of the present invention transduce sound of ultrasonic frequencies within the range of about 20 kHz to about 1000 kHz within the range of about 20 kHz to about 2000 kHz, within the range of about 20 kHz to about 5000 kHz, or within the range of about 20 kHz to about 10 MHz, but no more than about 20 MHz; more typically, from about 100 kHz to about 750 kHz, and still more typically, from about 250 kHz to about 750 kHz. The term "sonic" refers to sound of a frequency that is within the audible range of the human ear-generally up to about 20 kHZ—for example, between 20 Hz and 20 kHz.

As used herein, the term "cavitation" refers to the generation and/or stimulation of bubbles by sound. More specifically, the term "cavitation" is used herein to refer to the interaction between an ultrasonic field in a liquid and in gaseous inclusions (e.g., microbubbles) within the insonated medium. By "generation" is meant the creation of bubbles; by "stimulation" is meant the action that causes the bubbles to become dynamically active—that is, to move, to get bigger and smaller, to grow, to dissipate, all with associated mechanical and/or chemical effects in and around the fluid surrounding the bubbles and within the gas inside the bubbles.

Cavitation of existing microbubbles may be subdivided, to a first approximation, into two general categories— "stable cavitation" and "inertial cavitation." "Stable cavitation" is the induction of stable, low-amplitude, resonant oscillations of preexisting microbubbles by low-intensity ultrasound energy, which, in turn generates local shear forces within the fluid flow (referred to herein as acoustic microstreaming) near and adjacent to the microbubbles. As the ultrasound intensity is increased, the amplitude of oscillation also rises until the bubble becomes unstable and collapses due to the inertia of the inrushing fluid, giving rise to "inertial cavitation."

The resulting extremes of pressure and temperature within a violently collapsing bubble (one typically more active that those required for the present invention) can be sufficient to initiate free radical generation by hydrolysis of contained water vapor. If bubble collapse occurs in proximity to a fluid/solid interface (for example, a dental surface), shear forces within the medium and high velocity fluid jets are directed toward the solid structures, i.e., the teeth and gums. In the context of the present invention, cavitation effects include ultrasound-induced stimulation of microbubbles already present in the dental fluid due to the action of bristles into stable cavitation that, through the resulting scrubbing action from the shear forces associated with microstreaming, displaces or loosens plaque and other debris from dental surfaces and interproximal surfaces. Another effect can be the generation of coherent fluid flow away from the transducer, called acoustic streaming, whose strength is enhanced by the interaction of the ultrasound and microbubbles. Generally, microbubbles that undergo cavitation by the ultrasonic transducer of the present invention are between about 1 µm and about 150 µm in diameter.

Bubbles have a primary resonant frequency that varies inversely with the bubbles' radius, and also strongly depends on other factors, such as gas content and surface tension. Typically, for example, bubbles in dental fluid having a diameter of between about 1 µm and about 150 µm resonate when ultrasound is applied to those bubbles with an ultrasound transducer operating in the 20 kHz to 3 MHz range. More typically, bubbles in dental fluid having a diameter of between about 1 µm and about 100 µm resonate when ultrasound is applied to those bubbles with an ultrasound transducer operating in the 30 kHz to 3 MHz range. Still more typically, bubbles in dental fluid having a diameter of between about 4.3 µm and about 33 µm resonate when ultrasound is applied to those bubbles with an ultrasound transducer operating in the 100 kHz to 750 kHz range. Still more typically, bubbles in dental fluid having a diameter of between about 5 µm and about 30 µm resonate when ultrasound is applied to those bubbles with an ultrasound transducer operating in the 100 kHz to 600 kHz range. Still more typically, bubbles in dental fluid having a diameter of between about 6.5 µm and about 22 µm resonate when ultrasound is applied to those bubbles with an ultrasound transducer operating in the 150 kHz to 500 kHz range. In an exemplary toothbrush presented herein, bubbles in dental fluid having a diameter of between about 12 µm and about 26 µm resonate when ultrasound is applied to those bubbles with an ultrasound transducer operating in the 250 kHz to 500 kHz range. Whether or not the applied ultrasonic frequency differs from a bubble's resonant frequency, low levels of ultrasound will induce temporal variations in bubble volume, both within an acoustic cycle and over many acoustic cycles that are initially small and sinusoidal. Thus, "stable cavitation" refers to those simple volumetric changes in bubbles, where factors in addition to and/or instead of the inertia in the surrounding fluid govern the bubble behavior. And, whether or not the applied ultrasonic frequency differs from a bubble's resonant frequency, those induced temporal variations in bubble volume will generate movement within the fluid in proximity to the bubble, whose mechanical effects can remove plaque.

Due to geometric properties and impedance mismatch, cavitating bubbles scatter and emit sound. Compression and rarefaction of a bubble undergoing stable cavitation cause an emission of sound, primarily at the frequency of the applied signal for low levels of ultrasound. As bubbles grow toward their resonant frequency (which can happen in only a few cycles) or as the applied sound field increases, the volumetric changes in the bubble evolve to more complex functions of time within an acoustic cycle, as do the acoustic emissions, whether or not those changes remain radially symmetric. As a function of growing bubble amplitude, those emissions first include the superharmonics ($2F_0$, $3F_0$, etc.) of the applied signal ($F_0$) (as well as acoustic emissions of $F_0$ itself). Eventually, a once stabley-oscillating bubble may collapse violently and/or become asymmetric, with an associated increase in amplitude of the superharmonic emissions as well as broadband acoustic emissions (i.e., non-integral values of $F_0$) over a greater range of frequencies, including the eventual emission of multiples of the subharmonic of the applied signal (e.g., $(1/2)F_0$). By detecting these emissions—for example, via a hydrophon—the level of cavitation activity within insonified material can be remotely assessed and correlated with a variety of mechanical and chemical effects associated with cavitation, such as, for example, plaque removal, as demonstrated herein. See Chang et al., *IEEE Transactions on Ultrasonics, Ferroelectrics, and Frequency Control* 48(1):161-170 (2001); Poliachik et al., *Ultrasound in Medicine and Biology* 27(11): 1567-1576 (2001); Leighton, *Ultrasonics Sonochemistry* 2(2):S123-S136 (1995); and Roy et al., *J. Acoust. Soc. Am* 87(6):2451-2458 (1990). For example, when divided by the amplitude of the applied signal, one can expect the normalized amplitude of the superharmonics to increase as bubble activity increases, with associated increases in plaque removal. In addition, one can expect the integral over the spectral emission band (from $(1/2)F_0$ through $10F_0$, say) of the bubbly medium to increase as bubble activity increases, with an associated increase in plaque removal.

As used herein, the terms "microstreaming" and "acoustic microstreaming" refer to the movement of fluid near and adjacent to microbubbles that occurs as a result of the action of mechanical pressure changes within the ultrasonic field on the microbubbles. In the context of the present invention, germane to "microstreaming" and "acoustic microstreaming," are the shear forces associated with cavitating microbubbles within dental fluid that are distributed along the surfaces of the gums and teeth, as well as in interproximal and subgingival spaces. These shear forces, in turn, remove the plaque and/or stains on these surfaces.

Governing ultrasound parameters for "acoustic microstreaming" include (1) the carrier frequency (i.e., the frequency of the individual ultrasound waves) is generally above about 20 kHz. More typically, the carrier frequency is between about 30 kHz and about 3 MHz; more typically, the carrier frequency is between about 100 kHz and about 750 kHz; more typically, the carrier frequency is between about 100 kHz and about 600 kHz; more typically, the carrier frequency is between about 150 kHz and about 500 kHz; and, still more typically, the carrier frequency is between about 250 kHz and about 500 kHz—it will be understood that the actual value for the carrier frequency will depend upon the available bubble population and the size of ultrasound transducer employed; (2) the "pulse repetition frequency" (PRF) i.e., the frequency of packets or bursts of individual ultrasound waves, typically, though not exclusively, ranges from about 1 Hz and about 10,000 Hz; more typically between about 10 Hz and about 1,000 Hz, and still more typically between about 50 Hz and about 250 Hz it will be understood that the actual value for the PRF will be a small multiple (generally two or greater, more typically four or greater) of the sonic frequency (i.e., the frequency of movement of the bristles and/or acoustic waveguide driven by the sonic component of a toothbrush of the present invention); and (3) the number of individual ultrasound waves within a packet or burst of ultrasound is typically between about one and about 5,000; typically between about 5 and about 1000; more typically between about 5 and about 100. For acoustic microstreaming, short bursts and low PRF are suitable. The product of PRF and burst duration yields the duty cycle (i.e., the percentage of time that the ultrasound is on). Typically, the duty cycle is between about 1% and about 10%.

As used herein, the term "acoustic streaming" refers to the bulk or coherent flow of fluid that occurs due to momentum transfer from an acoustic wave to a fluid as a result of attenuation of an ultrasound beam. Ultrasound propagating into fluid, with or without bubbles, can generate "acoustic streaming," which can be quite significant in size and extent, and even greater with than without bubbles in the fluid. Acoustic streaming generally requires higher frequencies than required for stimulating the bubbles (the higher the frequency, the greater the acoustic streaming).

The acoustic streaming velocity, v is proportional to the amplitude absorption coefficient, a of the fluid (itself proportional to the frequency of the ultrasound under linear acoustic propagation conditions, and even more strongly dependent upon frequency under nonlinear acoustic propagation conditions), and inversely proportional to its kinematic viscosity, υ as follows:

$$v=(al^2I/cv)(G)$$

where I is the intensity in the beam of ultrasound and l the ultrasound beam diameter, c is the velocity of sound and G is a geometric factor that depends upon the size of the acoustic beam. Zauhar et al., *British J. of Radiology* 71:297-302 (1998).

Governing ultrasound parameters for "acoustic streaming" include (1) the carrier frequency is typically greater than about 20 kHz; more typically, between about 500 kHz and about 5,000 kHz or more, to enhance acoustic absorption; (2) the pulse repetition frequency (PRF) is typically, though not exclusively, between about 1 Hz and about 10,000 Hz; more typically between about 10 Hz and about 10,000 Hz; still more typically between about 100 Hz and about 10,000 Hz; and yet more typically, between about 1000 Hz and about 10,000 Hz; and (3) the number of individual ultrasound waves within a packet or burst of ultrasound is typically between 1 and 5,000; more typically between about 5 and about 100 waves. To enhance "acoustic streaming," longer duty cycles are typical, such as, for example, at least about 10%; more typically between about 25% and about 100%; still more typically between about 50% or about 75% and about 100%. Longer bursts, e.g., greater than about 100 waves at a frequency of about 1 MHz, with a PRF of at least 1000 Hz, are exemplified herein. It will be apparent, however, that different burst lengths, frequencies, and PRF values may be suitably employed in toothbrushes of the present invention.

As used herein, the term "mechanical index" refers to a measure of the onset of cavitation of a preexisting bubble subjected to one cycle of applied acoustic pressure. Holland et al., *IEEE Transactions on Ultrasonics, Ferroelectrics, and Frequency Control* 36(2):204-208 (1989); and Apfel et al., *Ultrasound Med. Biol.* 17(2):179-185 (1991). This measure is proportional to the peak negative pressure (MPa) amplitude and inversely proportional to the square root of the frequency (MHz) of the applied sound. When the value of mechanical index exceeds 1.9, it is possible for ultrasound to produce inertial cavitation, the most mechanically active type of cavitation, and in excess of the amount required to remove plaque. The governing assumptions require isothermal growth of an optimally sized bubble, the neglect of gas diffusion into the bubble, and that the fluid surrounding the bubble is incompressible. These three assumptions produce the most active bubble collapse, making the mechanical index a conservative measure of the onset of inertial cavitation.

Empirical evidence indicates that plaque removal may be achieved with mechanical indices as low as 0.1. Theoretical considerations, however, suggest that plaque reduction may be achieved with mechanical indices as low as 0.01. Krasovitski et al., *IEEE Transactions on Ultrasonics, Ferroelectrics, and Frequency Control* 51(8):973-979 (2004). For example, the shear stress on a wall created by acoustic microstreaming associated with a bubble suspended in water and subjected to ultrasound at a frequency of 430 kHz and pressure amplitude of 10,000 Pa (e.g., a mechanical index of approximately 0.01) is predicted to be approximately 5 Pa, which is sufficient to remove plaque via steady flow over plaque. Stoodley et al., *J. Industrial Microbiology & Biotechnology* 29:361-367 (2002). The mechanical indices delivered by toothbrushes of the present invention are generally in the range of about 0.001 to about 1000. More typically, mechanical indices are in the range of about 0.001 to about 100, still more typically in the range of about 0.002 to about 20, and even more typically in the range of about 0.01 to about 5, or between about 0.01 and about 1.9.

As used herein, the term "microbubble" refers to microscopic bubbles present in the oral cavity, for example, in the dental fluid or plaque. "Microbubbles" may be endogenous to the fluid, such as through the introduction of an appropriate dentifrice; may be generated by toothbrush bristles through manual brushing; and/or may be generated by bristles in combination with the sonic component of certain of the presently disclosed power toothbrushes. "Microbubbles" are acted upon by an ultrasonic signal transmitted by an ultrasonic transducer and propagated by an acoustic waveguide. "Microbubbles" resonate at or near a specific frequency depending upon the microbubbles' diameter.

An Exemplary Toothbrush

FIG. 1 shows an exemplary toothbrush 10 according to the present invention. The toothbrush 10 comprises a handle 15 constructed of a rigid or semirigid material, and typically houses a rechargeable battery 12 that is preferably adapted to be induction charged electrical circuitry, including an ultrasonic module drive circuit 14; a sonic component 16 comprising a motor, preferably a DC motor for driving a toothbrush head 20 at sonic frequencies; and a timer and motor control unit 18. Suitable motors, ultrasonic drive circuits, rechargeable batteries, and timer and motor control units are well known in the art.

Attached to the handle 15 is a toothbrush head 20, including a stem portion 21 and further comprising an ultrasonic transducer 22 and an acoustic waveguide 24 in operable proximity to the ultrasonic transducer. In the toothbrush embodiment presented in FIG. 1, a foam element 28 is shown behind, and extending around each side of, the ultrasonic transducer 22. It will be appreciated that the foam element 28 will at least partially reflect the ultrasound forward through the acoustic waveguide 24 and into the dental fluid. The toothbrush head 20 may be either removably or fixedly attached to the handle 15. In general, the toothbrush head 20 includes a plurality of bristle tufts 26 disposed adjacent to the acoustic waveguide 24. The toothbrush head 20 may optionally include an impedance matching layer 29. The impedance matching layer 29 improves the efficiency of the device, as discussed below.

In the disclosed embodiment, alternating current supplied by the ultrasonic module drive circuit 14 drives the ultrasonic transducer 22 such that the transducer 22 expands and contracts primarily along one axis at or near resonance with the frequency supplied by the ultrasonic module drive circuit 14, thereby converting electrical energy into ultrasonic energy. The resulting ultrasonic sound waves are conducted into, propagated through, focused by, and radiated out of the acoustic waveguide 24. The focused ultrasonic energy acts on microbubbles within the dental fluid (typically saliva and dentifrice, not shown) to induce cavitation, thereby loosening plaque deposited on the teeth and interproximal regions.

The Ultrasonic Transducer

As described above, certain embodiments of the present invention provide a toothbrush 10 that employs an ultrasound transducer 22 to generate ultrasonic energy in combination with an acoustic waveguide 24 to efficiently propagate that ultrasonic energy into the dental fluid. Microbubbles, either present in the dental fluid through conventional, manual brushing action with a manual toothbrush and/or formed by action of a sonic component 16 driving the motion of the toothbrush bristles 26 and/or acoustic waveguide 24 at sonic velocities (see below), are stimulated through ultrasonic energy-induced cavitation to achieve "scrubbing bubbles" that are effective in loosening and removing plaque from a tooth surface and interproximal regions at a finite distance from the toothbrush head.

Absent the ultrasonic transducer 22 of the present invention, microbubbles are simply passive voids within the dental fluid. The ultrasonic transducer 22 disclosed herein causes these microbubbles to pulsate, thereby generating local fluid motion around the individual bubbles. This effect is referred to herein as "microstreaming" and, in combination with the ultrasonic cavitation effects, achieves shear stresses that are sufficient to disrupt plaque. Typically, shear stresses achieved by microstreaming induced by the ultrasonic transducer 22 of the present invention, are between about 0.1 Pa and about 1000 Pa. More commonly, shear stresses achieved by microstreaming are between about 0.2 Pa and about 500 Pa. Still more commonly, shear stresses are between about 0.3 Pa and about 150 Pa. And most commonly, shear stresses are between about 1 Pa and about 30 Pa.

Another effect of the ultrasonic transducer 22 is the deposition of momentum within the dental fluid in a direction toward the teeth and interproximal and subgingival spaces, thereby increasing the velocity and coherency of the dental fluid. This bulk fluid-flow process is referred to herein as acoustic streaming.

Either through the generation of acoustic microstreaming and/or acoustic streaming, the associated shear and pressure forces act to erode and dislodge the plaque in a manner and to an extent that is in excess of that achieved by the toothbrush bristles 26 alone. In particular, these ultrasonic effects are facilitated by propagating the ultrasonic waves from the ultrasonic transducer 22 through an acoustic waveguide 24 and into the dental fluid near and beyond the bristle tips 26.

Ultrasonic transducers 22 that may be suitably employed in the ultrasonic toothbrush 10 of the present invention are readily available in the art (see, for example, U.S. Pat. No. 5,938,612 and No. 6,500,121, each of which is incorporated herein by reference in its entirety) and, most commonly, operate either by the piezoelectric or magnetostrictive effect. Magnetostrictive transducers can, for example, produce high intensity ultrasonic sound in the 20-40 kHz range. Alternatively, ultrasound may be produced by applying the output of an electronic oscillator to a thin wafer of piezoelectric material, such as lead zirconate titanate (PdZrTi or PZT). There is a wide variety of piezoelectric PZT ceramic blends that can be used to fabricate ultrasonic transducers suitable for use in the toothbrushes of the present invention. Other transducer materials, such as piezopolymers, like single or multilayer polyvinylidene fluoride (PVDF), or crystalline piezoelectric materials, such as lithium niobate ($LiNbO_3$), quartz, and barium titanites, may also be used. Ultrasound transducers may be flat or curved (as, e.g., in a conic section) to focus the ultrasonic waves.

In addition to piezoelectric materials, capacitive micromachined ultrasonic transducer (cMUT) materials or electrostatic polymer foams are also suitable. Many of these materials can be used in a variety of vibrational modes, such as radial, longitudinal, shear, etc., to generate the acoustic waves. In addition, single-crystal piezoelectric materials, such as $Pb(Mg_{1/3}Nb_{1/3})O_3$—$PbTiO_3$ (PMN-PT) and others, may be used to reduce voltage/transmit-level ratios by as much as an order of magnitude.

In addition to the transducer materials, one or multiple impedance matching layers 29 (typically designed as quarter-wave matching layers) can help to improve the efficiency and bandwidths when transmitting from the commonly high-impedance transducer materials into the much lower impedance acoustic waveguide materials. Generally, a matching material is chosen with a thickness that will support a quarter wave of the desired frequency and an acoustic impedance optimally selected within the two impedances to be matched. Appropriate materials can include materials such as epoxy and metal particulate composites, graphite, or a host of other candidate materials known by and readily available to the skilled artisan.

The Acoustic Waveguide

As indicated above, one aspect of the present invention is based upon the observation that an acoustic waveguide used in operable combination with an ultrasonic transducer is effective in propagating ultrasonic waves from the transducer into the dental fluid, thereby generating and/or causing cavitation of microscopic bubbles (microbubbles) present within the dental fluid. Typically, as shown in FIG. 1, the ultrasonic transducer 22 is positioned at the base of the toothbrush head 20, in operable proximity to the acoustic waveguide 24, such that ultrasonic waves are efficiently propagated into and through the acoustic waveguide 24 and into the dental fluid (not shown).

As noted above, within certain embodiments, the present invention also provides power toothbrushes 10 comprising a toothbrush head 20 having an acoustic waveguide 24 wherein the toothbrush head 20 is operably connected to a sonic component 16 and wherein the sonic component 16 causes the acoustic waveguide 24 to vibrate so as to increase the flow of and generation of microbubbles in the dental fluid into which the acoustic waveguide 24 is immersed.

Within still further embodiments are provided power toothbrushes 10 comprising a combination of an acoustic waveguide 24 in operable proximity to an ultrasound transducer 22 and in operable connection with a sonic component 16 to achieve still further improved dental cleaning properties owing to the combined increase in fluid flow and microbubble formation, as well as cavitation and acoustic microstreaming effects. Here, operable connection can be facilitated by putting the ultrasonic transducer 22 in direct contact with the acoustic waveguide 24 or, alternatively, ultrasound conducting material such as an impedance matching layer 29 can be placed between the ultrasonic transducer 22 and the acoustic waveguide 24 both to increase the efficiency of ultrasound transmission from the transducer 22 into the acoustic waveguide 24 or, alternatively or additionally, to usefully increase the distance between the transducer 22 and the acoustic waveguide 24 to facilitate the manufacturing process of the device, for example.

Rigid acoustic waveguides, such as solid waveguides made from aluminum or titanium and hollow waveguides filled with degassed water have been described for the delivery of high intensity focused ultrasound (HIFU) into living tissue for therapeutic purposes (such as drug delivery and hemostasis) via heat induction and/or for the generation of inertial cavitation. See, e.g., U.S. Patent Publication No. 2003/0060736 to Martin et al. and Mesiwala et al., *Ultrasound in Medicine and Biology* 28(1):389-400 (2002).

These applications for acoustic waveguides demonstrate the use of a physical member to facilitate propagation of ultrasound beyond the face of an ultrasound transducer to achieve therapeutic benefit. The present invention is, in contrast, based upon the observation that acoustic waveguides having a flexible member, typically having a flat profile, may be employed in combination with an ultrasound transducer to facilitate propagation of ultrasound into the oral cavity to stimulate existing bubbles to remove plaque in a way that also optimally generates a bubbly fluid jet (due to the flat aspect of the profile) and promotes a favorable mouth feel.

The dental fluid into which the acoustic waveguide 24 (FIG. 1) is immersed is typically a saliva and toothpaste emulsion that is very acoustically absorptive due to the presence of large air pockets within individual bristle tufts 26 and between neighboring bristle tufts 26 and, without the use of an acoustic waveguide 24, would attenuate significant amounts of the ultrasound before the wave front reached the tooth and gum surfaces. The air medium has very low acoustic impedance, which creates a large impedance mismatch with the high acoustic impedance materials generally used in the ultrasonic transducer 22. This impedance mismatch is a significant barrier to sound transmission from the ultrasonic transducer 22 to the tooth and gum surfaces. The acoustic waveguide 24 serves as a bridge across this acoustic mismatch by accepting, containing, and transmitting the acoustic energy into the saliva and toothpaste emulsion near the tooth surface, thereby overcoming the attenuation effect normally encountered by the saliva and toothpaste emulsion.

A variety of acoustic waveguide designs are contemplated by the present invention as exemplified by the acoustic waveguides diagramed in FIGS. 2-5 and 9A-9H. Depending upon the precise embodiment of the present invention, the acoustic waveguide 24 may be used alone, in combination with the sonic component 16, and/or in combination with the ultrasonic transducer 22. Suitable acoustic waveguides have in common the capacity to physically move the dental fluid and/or to efficiently facilitate the propagation and possibly the focusing of ultrasonic waves transmitted by the ultrasonic transducer 22, thereby enhancing fluid motion and the associated effects of the resulting cavitation and microstreaming.

Figure 2B:
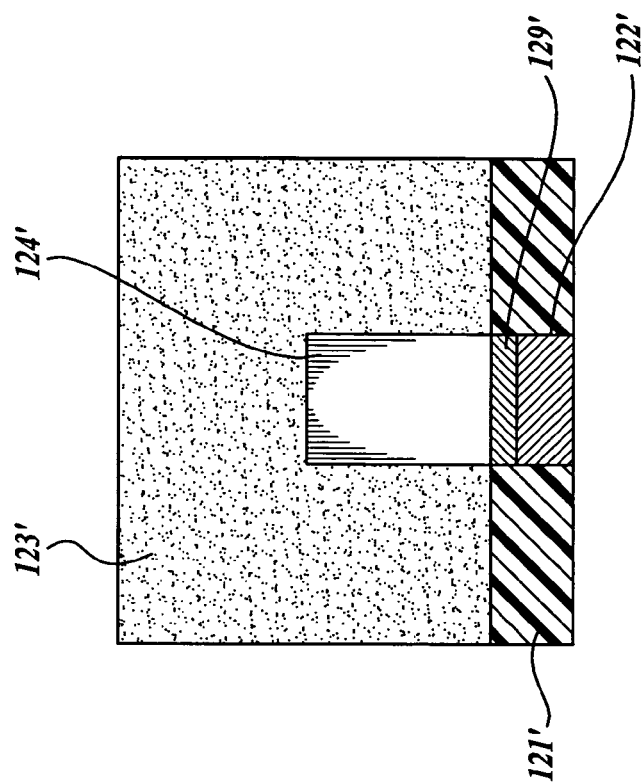
FIG. 2B is a diagram depicting a finite element model simulation geometry of the exemplary toothbrush head shown in FIG. 2A (shown here without bristles)
Figure 2A:
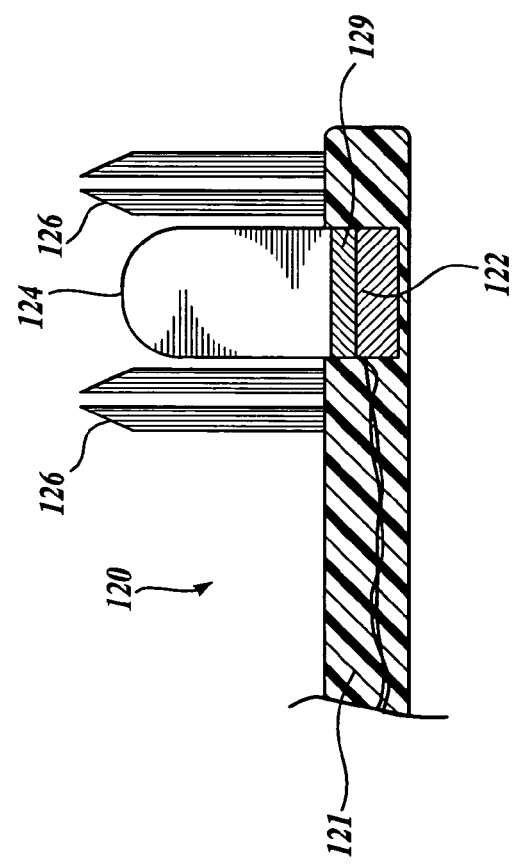
FIG. 2A is a diagram depicting a cross-sectional view of an exemplary power toothbrush head similar to the embodiment illustrated in FIG. 1, showing a handle, bristles, an ultrasonic transducer, and an acoustic waveguide shaped generally as a rectangular solid.
Figure 2D:
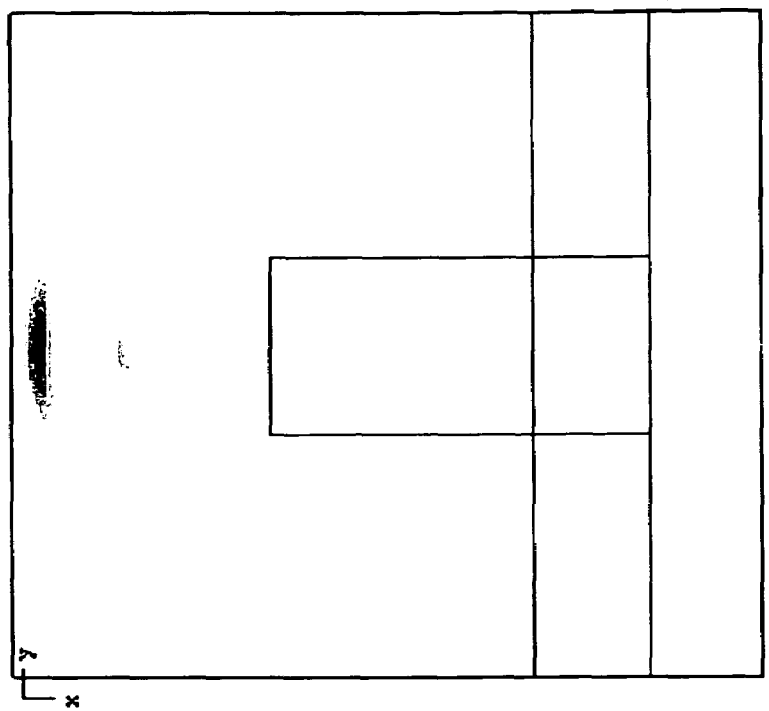
FIG. 2D is a diagram depicting the simulated ultrasound wave field at 2.0 ms post-pulse, wherein the ultrasonic waves have substantially left the acoustic waveguide.
Figure 2C:
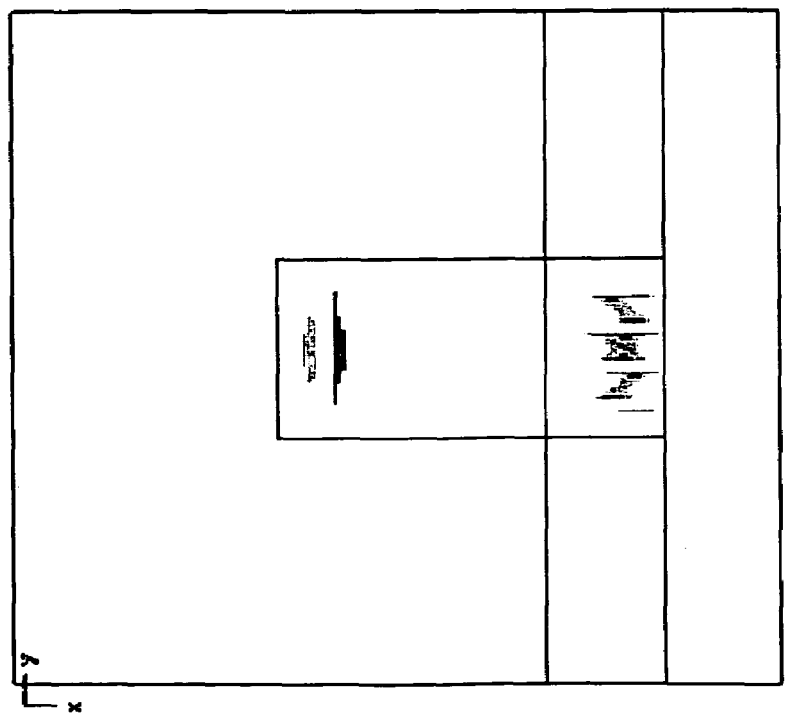
FIG. 2C is a diagram depicting the simulated ultrasound wave field at 1.2 ms post-pulse wherein the ultrasonic waves remain mainly in the acoustic waveguide.
Figure 3D:
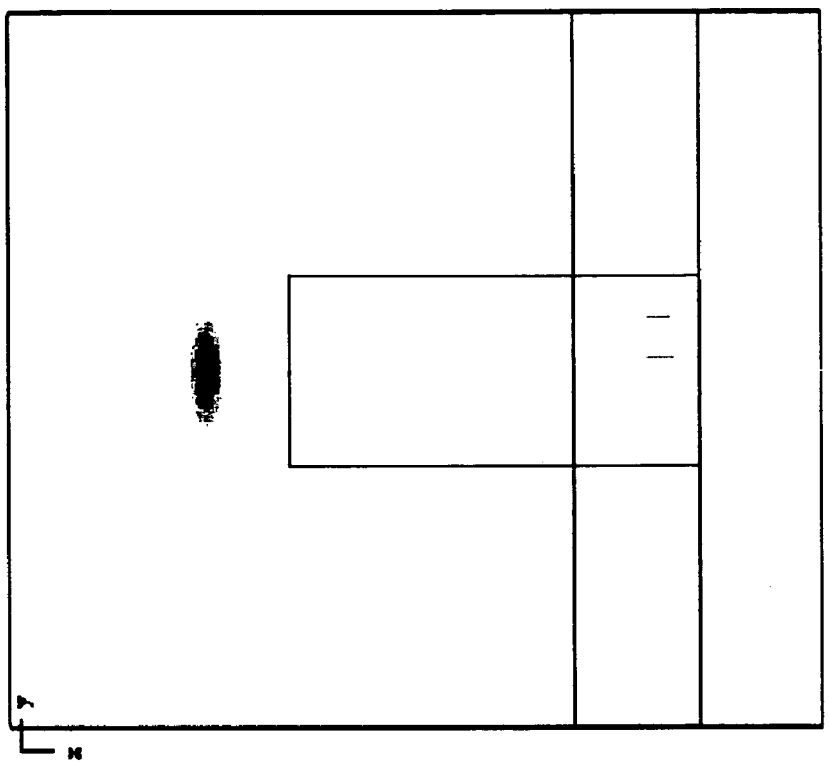
FIG. 3D is a side view of the simulated wave field plot at a later time subsequent to ultrasonic transmission showing acoustic waveguide propagation of the ultrasonic wave front into the fluid emulsion.
Figure 3C:
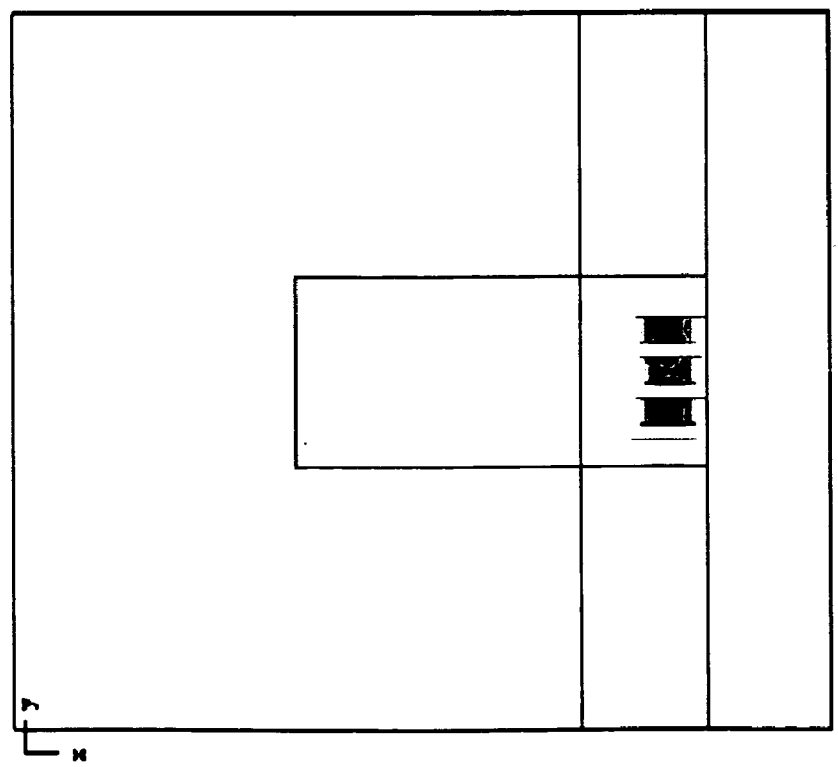
FIG. 3C is a side view of the simulated wave field plot soon after ultrasonic transmission, showing propagation within the acoustic waveguide.
Figure 3F:
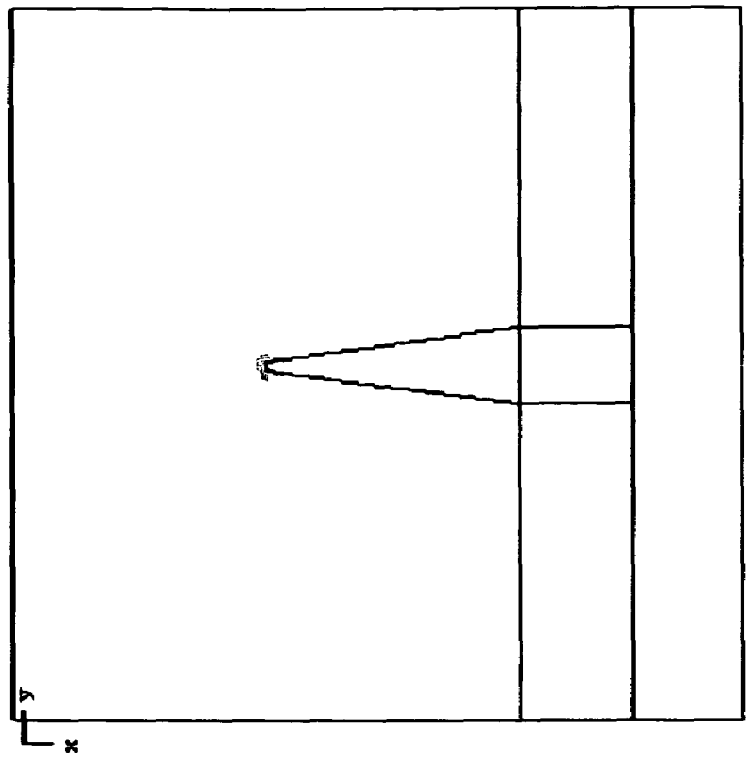
FIG. 3F is an end view of the simulated wave field plot at the same simulation time as FIG. 3D.
Figure 3E:
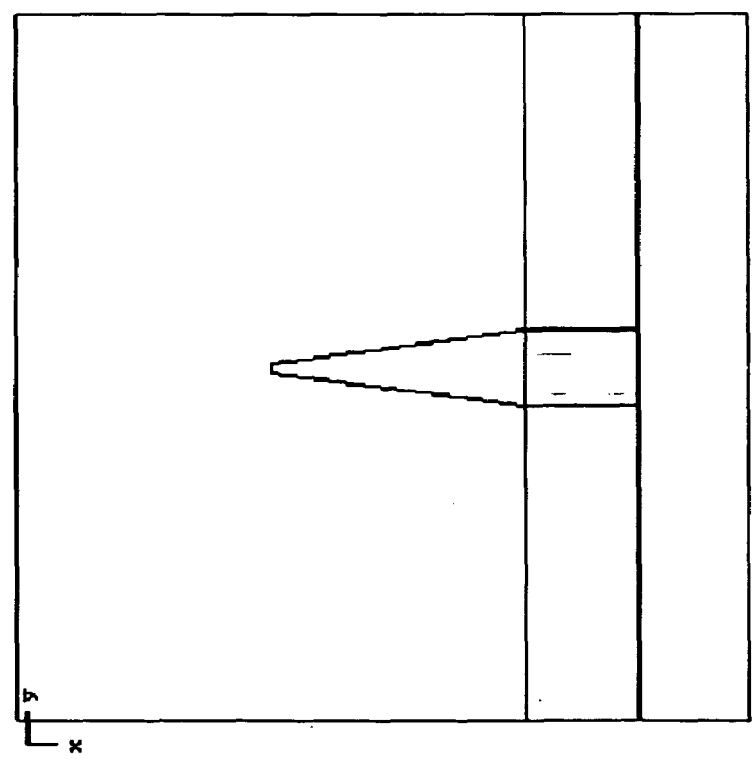
FIG. 3E is an end view of the simulated wave field plot at the same simulation time as FIG. 3C.
Figure 4B:
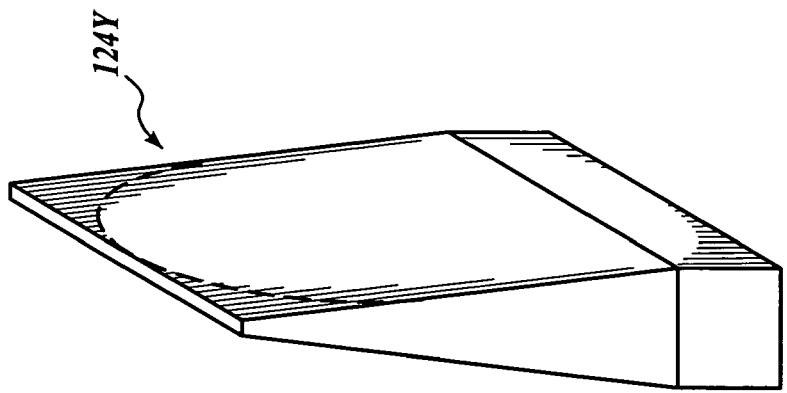
FIG. 4B is a perspective view of the waveguide shown in FIG. 4A, wherein the portion beyond the curved dotted line is removed.
Figure 4A:
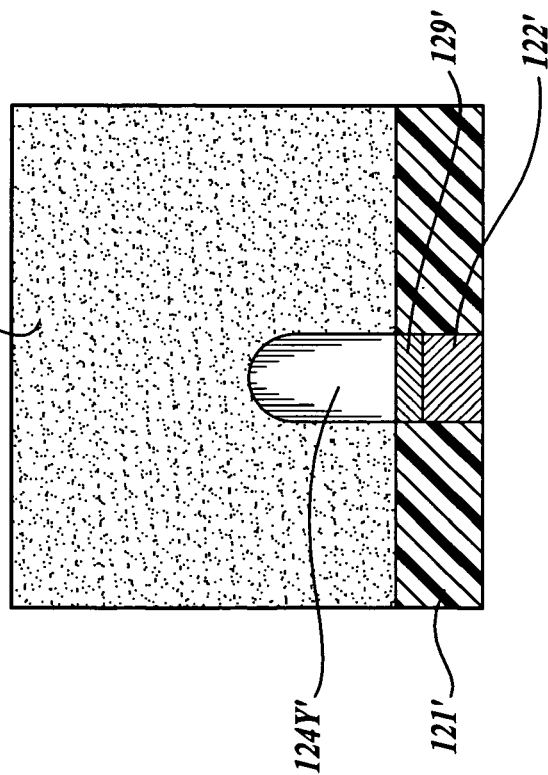
FIG. 4A is a finite element model simulation geometry of another exemplary acoustic waveguide, wherein the waveguide tip is curved.
Figure 4D:
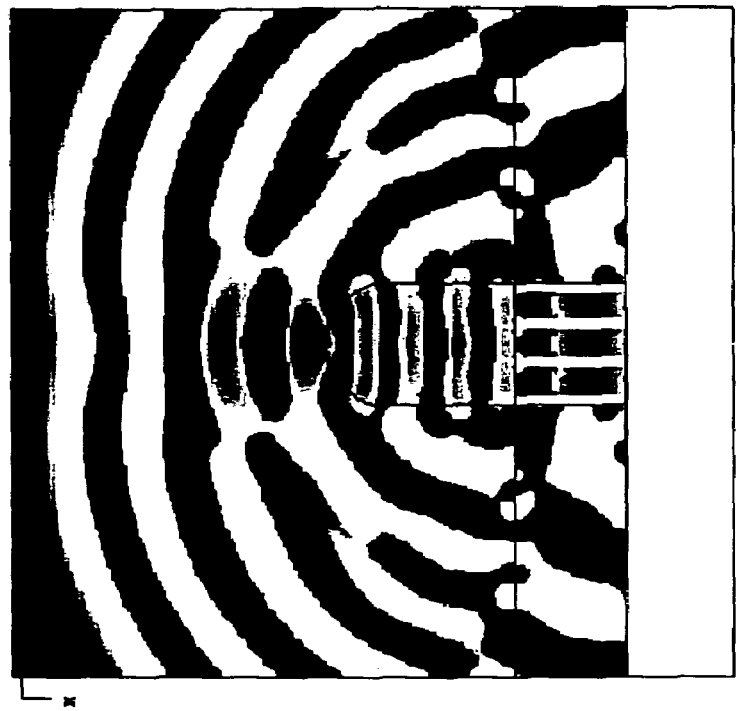
FIG. 4D is a wave field plot at a later time subsequent to ultrasonic transmission showing the focusing of the ultrasonic wave front beyond the tip of the acoustic waveguide and propagation of that ultrasonic wave front into the fluid emulsion.
Figure 4C:
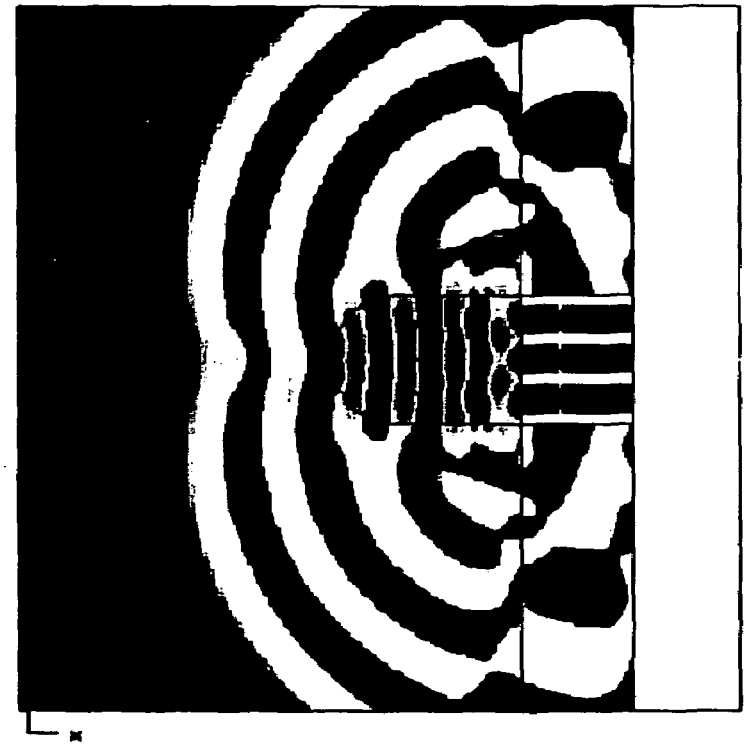
FIG. 4C is the simulated wave field plot soon after ultrasonic transmission, showing propagation within the acoustic waveguide.

FIG. 2A shows an embodiment of an exemplary power toothbrush head 120 comprising an ultrasonic transducer 122 in combination with an acoustic waveguide 124. The side view shows the acoustic waveguide 124, which carries the ultrasonic energy from the ultrasonic transducer 122 to the teeth and gums (not shown). Acoustic waveguide 124 is in operable proximity to the ultrasonic transducer 122 and adjacent to and flanking on one or more sides bristle tufts 126. In this exemplary design, the acoustic waveguide 124 is made from a soft, smooth silicone rubber, known for both its pleasant surface texture and ability to transmit ultrasound and an impedance matching layer 129 is disposed between the acoustic waveguide 124 and the ultrasonic transducer 122.

The two parameters that most substantially affect the transmission of ultrasonic waves through an acoustic waveguide are (1) the material out of which the waveguide is fabricated, and (2) the geometry of the waveguide. Each of these parameters is described in further detail herein. Regardless of the precise acoustic waveguide material and geometry employed, the present invention contemplates the selection of such parameters to achieve a favorable mouth feel. Thus, the material out of which the acoustic waveguide is fabricated or molded is preferably soft enough to be appealing when placed within the mouth and/or direct contact with the mouth. As will be appreciated by one skilled in the art, an acoustic waveguide with an appealing texture is ideally designed to efficiently couple in, conduct, coherently focus, incoherently compress, and couple out the acoustic energy.

The selection of suitable materials for fabricating an acoustic waveguide for use in a toothbrush of the present invention can be readily achieved by the skilled artisan in consideration of the following guidelines. Various dielectric materials, such as silicon dioxide ($SiO_2$), silicon nitride ($Si_3N_4$), and many polymers can be used as the waveguide material. For example, silicone castable/moldable RTV, liquid injection-molded (LIM) silicone, and/or thermal plastic elastomer (TPE) injection-molded processes may all be used. Polymers have an advantage over other waveguide materials, owing to their relatively low shear wave velocity.

However, because of their viscoelasticity, cross-linking may be necessary to avoid excessive acoustic loss. Cross-linking allows the acoustically lossy polymer to exhibit an equilibrium elastic stress, thus representing a stable waveguide layer.

The hardness of materials suitable for use in acoustic waveguides of the present invention may be determined by either the Shore (Durometer) test or the Rockwell hardness test. Both of these hardness test methodologies are well known and readily available in the art. These tests measure the resistance of materials to indentation and provide an empirical hardness value. Shore hardness, using either the Shore A or Shore D scale, is the preferred method for rubbers/elastomers and is also commonly used for "softer" plastics, such as polyolefins, fluoropolymers, and vinyls. The Shore A scale is used for "softer" rubbers, while the Shore D scale is used for "harder" ones. Shore hardness is measured with a Durometer and, consequently, is also known as Durometer hardness. The hardness value is determined by the penetration of the Durometer indenter foot into the sample. The ASTM test method designation is ASTM D2240 00. Related methods include ISO 7619, ISO 868, DIN 53505, and JIS K 6253. Each of these Durometer test methodologies is hereby incorporated by reference in their entireties.

The Durometer measurement of elastomeric acoustic waveguides will generally range in hardness from 5 to 110 Shore A, more typically from 10 to 100 Shore A, and still more typically from 20 to 80 Shore A. It will be apparent to the skilled artisan that harder materials may be employed in the acoustic waveguides used in conjunction with the power toothbrushes of the present invention; however, harder materials may provide a progressively unpleasant mouth feel.

The present invention also contemplates that more than one material may be used in combination to achieve acoustic waveguides having preferred properties of hardness and mouth feel. For example, additional acoustic matching elements may be embedded or stratified within the acoustic waveguide structure and be in operable contact with the ultrasonic transducer via one or more matching layers. Within certain embodiments, acoustic waveguides of the present invention further provide a matching layer at the waveguide tip to help coupling into low impedance toothpaste emulsions (e.g., dental fluid). Ideally, there will also be a significant specific acoustic impedance change between the sides of the acoustic waveguide and the surrounding medium such that the waves are not coupled substantially into the surrounding medium by the sides of the acoustic waveguide.

Exemplified herein are prototype transducer assemblies having a graphite impedance matching layer in operable contact with the PZT ultrasonic transducer. As shown in FIG. 9A, a waveguide assembly 150A may include a graphite core portion 152A or similar material that may be inserted into an injection mold, and an elastomer outer portion 154A molded around it via the process of insert molding. Alternatively, a multishot may be used to create a gradient of materials with different acoustic and elastomeric properties. As used herein, the term "multishot" refers to the placement of several shots of plastic into one mold. This process may be employed, for example, in acoustic waveguide embodiments in which a first relatively hard material layer (e.g., about Shore 80 hardness or greater) is in operable proximity to the ultrasonic transducer element; a second, relatively soft material layer (e.g., between about Shore 20 and Shore 80) is immediately adjacent to and in contact with the first material layer; and a third, still softer (e.g., about Shore 20 hardness or less) material layer is immediately adjacent to and in contact with the second layer, for a very gentle feel against teeth. These exemplary acoustic waveguide designs may either be formed as individual pieces or, alternatively, they may be molded in combination with the main hard toothbrush material.

Thus, within certain embodiments, acoustic waveguides of the present invention may comprise two or more plastic/elastomer layers. For example, acoustic waveguides comprising three, four, and/or five plastic/elastomer layers are contemplated for certain applications. Such acoustic waveguides may further comprise one or more inserted pieces for shaping the acoustic properties and optimizing sonic properties. Within still further embodiments, the acoustic waveguide may comprise one or more toothbrush bristles, either molded in combination with the plastic/elastomer and insert layers or attached following the molding process. Toothbrush bristle design and materials are well known and readily available to those of skill in the art.

Referring now to FIGS. 9A-9H, it will be appreciated by the artisan that acoustic waveguides may be formed in any of a variety of three-dimensional shapes or geometries. For example, FIG. 9A shows a waveguide 150A having a generally curved and tapered geometry. FIG. 9B illustrates an alternative waveguide 150B having a converging or wedge-shaped portion 152B. FIG. 9C shows an alternative waveguide 150C, wherein a converging portion is comprised of a plurality of shorter sections 152C that may be separated by gaps 154C. FIG. 9D shows an alternative waveguide 150D having a bullet-shaped body 152D with minor protuberances 154D to promote fluid flow. FIG. 9E shows an alternative waveguide 150E having a converging portion 152E having a curved end 154E. It will be appreciated that, although a simple curved end 154E is shown, it may be desirable in some circumstances to provide a more complex curved end portion. FIG. 9F shows an alternative waveguide 150F that is conically shaped. FIG. 9G shows an alternative waveguide 150G that is biconical. FIG. 9H shows an alternative waveguide 150H having a plurality of pyramid-shaped portions 152H. Certain design considerations regarding selection of an appropriate waveguide geometry will now be discussed. The shape of the waveguides may be selected, for example, to achieve a particular compression and/or focusing of the acoustic waves.

Within certain embodiments of the present invention, acoustic waveguides are capable of acoustic coherent focusing of the ultrasonic waves transmitted from the ultrasonic transducer. Acoustic coherent focusing may be achieved, for example, by curving the waveguide tip wherein the tip comprises a conductive medium having a known sound speed. Alternatively, a section of ultrasound-conducting polymer having a known wave speed may be added to the end of a curved waveguide to nearly complete focusing before entering a medium of variable sound speed (e.g., dispersive bubbly medium). Within such embodiments, a single curve may be employed to achieve a single focus, whereas a scalloped curve is useful for producing multiple foci.

Within alternative embodiments, acoustic waveguides are capable of acoustic incoherent focusing of the ultrasonic waves transmitted from the ultrasonic transducer. Acoustic incoherent focusing may be achieved, for example, by conical or wedge shapes that conduct sound into a progressively smaller area in a semicoherent manner such that intensity increases. Alternatively, multiple conical tips may be employed to provide multiple areas of higher acoustic intensity.

Regardless of the precise material and/or geometry, acoustic waveguides of the present invention are fabricated to generate fluid flow when moved on a toothbrush head. The desired fluid motion and transmission of ultrasound into the dental fluid may be achieved, for example, by employing a flexible mechanical protrusion that extends into the dental fluid. In such cases, motion of the acoustic waveguide may be side-to-side or rotational.

When acoustic waveguide motion is rotational, the motion may be generally about or parallel to a longitudinal axis of the waveguide and may be achieved with a wedge or cone, multiple wedges or cones in cross or star patterns, a pinwheel, and/or multiple wedges in a star pattern without a center. Alternatively, rotational motion may be about the axis along the toothbrush head, as may be achieved with a wedge- or rectangular-shaped acoustic waveguide.

Suitable acoustic waveguides may also adopt a propeller-like geometry such as a standard propeller design or a spiral design. Alternatively, an acoustic waveguide may have a hinged hydrofoil-like shape wherein its motion creates fluid lift and consequent fluid flow.

Acoustic waveguides can also be designed to increase the intensity of acoustic energy delivered to the surface of the teeth and gums. For example, an acoustic waveguide can be designed to contain and compress the propagating acoustic energy into a smaller physical area. If the waveguide is designed with materials of low acoustic attenuation and with appropriate sound speed, the quantity of energy delivered from the end of the waveguide will be comparable to that transmitted into the waveguide, but can be compressed into a smaller area and will therefore have a higher energy density and/or acoustic intensity. Waveguide tip motion creates an "acoustic painting" effect to broadly distribute acoustic energy.

In addition to low attenuation, waveguides are generally designed to channel the acoustic energy along the waveguide, and transmit or "leak" a minimum of acoustic energy into the surrounding medium before it has propagated to the end of the waveguide. One method for achieving this is to use a material having a sound speed substantially lower than the surrounding fluid and having shallow slopes on the sides of the waveguide (e.g., wedge shaped). The shallow slope of the waveguide walls causes the propagating waves to contact the waveguide and fluid interface at low grazing angles. Because the wavelength in the waveguide is shorter than that of the surrounding medium, the waves will only couple into less efficient subharmonic modes where the launch angle is defined by the ratio of multiples of wave guide wavelengths to surrounding media wavelengths. These poorly coupled modes of transmission into the fluid do not extract large amounts of energy from the waveguide.

The combination of containing, transmitting, and compressing acoustic energy enables the generation of high intensity acoustic fields at the waveguide tip and improves the efficiency of acoustic energy delivery. Therefore, lower electrical power levels are required to generate appropriate acoustic intensities for bubble activation. FIGS. 2A-2D (for a rectangular waveguide (124), FIGS. 3A-3F (for a wedge-shaped waveguide 124X), and FIGS. 4A-4D (for a wedge-shaped waveguide having a curved end 124Y) show finite element model and simulation results illustrating waveguides designed to compress the acoustic field. FIG. 2A shows a general, simplified model of a toothbrush head 120 according to the present invention, as discussed in detail above. FIG. 2B shows the corresponding portions of the finite element model used to model the toothbrush head 120, including a stem 121', an ultrasonic transducer 122', an impedance matching layer 129', and a waveguide 124'. Plots showing the wave field soon after transmission showing propagation in the waveguide are shown in FIGS. 2C, 3C, 3E, and 4C for selected waveguides. These figures evidence a low level of leakage into the surrounding fluid. FIGS. 2D, 3D, 3F, and 4D show a wave field plot later, after transmission, at which time the ultrasonic wave front is compressed into the tip of the waveguide and the transmission into fluid emulsion is primarily from the waveguide tip.

In addition to increasing the acoustic intensity delivered by compressing the acoustic field, the waveguide can be designed to coherently focus energy into surrounding media beyond the tip of the waveguide. This is accomplished by shaping the end of the acoustic waveguide to create an acoustic lens effect that will focus the waves from the waveguide into a higher intensity field beyond the waveguide. This focusing effect can be achieved with one or multiple waveguide materials combined together and shaped to create a focused field. For instance, a low attenuation, higher sound speed material may be used at the end of the waveguide to continue propagating and focusing the wave front before the wave front emerges into the higher attenuation toothpaste emulsion. As with the acoustic field compression described above, the increased acoustic intensity achieved with the focusing effect improves the device efficiency. Therefore, size, weight, power, and costs are reduced and battery life is extended for a final device.

Still further embodiments provide that the acoustic waveguide may be configured to exhibit improved fluid propulsion properties when used in a power toothbrush head in combination with a sonic component (see below) either with or without an ultrasonic component.

The Sonic Component

Within certain embodiments, toothbrushes of the present invention comprise a sonic component 16 (see, FIG. 1) in combination with the acoustic waveguide 24 and/or ultrasonic transducer 22, described above. Typically, a sonic component 16 comprises a motor assembly that generates sonic vibrations that are transmitted to the toothbrush head, thereby causing vibration of the acoustic waveguide 24 and/or bristle tufts 26. Such sonic vibrations generate bubbly flow within the dental fluid. For example, by employing a sonic component 16, the acoustic waveguide 24 can be made to lift and push dental fluid towards the teeth as well as interproximal and subgingival spaces, with an associated fluid flow of sufficient pressure and shear force to cause the erosion of plaque. A vibrating acoustic waveguide 24 of the present invention is capable of moving fluid, including bubbly fluid, with sufficient velocity and focus to achieve plaque removal from teeth several millimeters beyond the bristles 26 of the toothbrush head 20. Motor assemblies that may be suitably employed in the toothbrushes of the present invention are well known and readily available to those of skill in the art, and are exemplified by the toothbrush head drive mechanisms presented within U.S. Pat. No. 5,987,681, No. 6,421,865, No. 6,421,866, No. RE 36,669, and U.S. Patent Publications No. 2002/0095734, No. 2002/0116775, No. 2002/0124333, and No. 2003/0079304. Each of these U.S. Patents and Patent Applications is hereby incorporated by reference in their entireties.

Toothbrushes of the present invention are capable of generating fluid flows at a range of about 1 cm/sec to about 50 cm/sec at a distance of between about 1 mm and 10 mm beyond the toothbrush bristle tips and/or acoustic waveguide. More typically, toothbrushes of the present invention are capable of generating fluid flows at a range of about 2 cm/sec to about 30 cm/sec at a distance of between about 1 mm and 10 mm beyond the toothbrush bristle tips and/or acoustic waveguide. Exemplified herein are toothbrushes that are capable of generating fluid flows of about 10 cm/sec at a distance of between about 1 mm and 10 mm beyond the toothbrush bristle tips and/or acoustic waveguide.

It will be recognized by those skilled in the art that the generation of bubbly flow by the sonic actions on the acoustic waveguide 24 does not require the ultrasonic component 16 described above. It is, however, the combination of the ultrasonic transducer 22, acoustic waveguide 24, and sonic component 16 that together comprise a toothbrush head 20 in either removable or fixed combination, with a handle 15 to achieve the most effective power toothbrush embodiment of the present invention. It is this combination of sonic and ultrasonic components that yields the most surprising benefits of improved microscopic bubbly flow properties in combination with enhanced cavitation and acoustic microstreaming. These physical properties provide superior cleaning properties of this embodiment of the present invention. That is, the ultrasonic and sonic components, when used in combination to achieve toothbrush designs disclosed herein, yield synergistic cleaning effects that are substantially superior to the additive effects of the sonic and ultrasonic components in isolation. For example, the acoustic waveguide 24 can be optimized to move bubbly fluid whose bubbles could facilitate acoustic streaming (thereby further enhancing the fluid flow generated by the waveguide alone) as well as acoustic microstreaming and cavitation.

Dentifrice Design and Compositions

Within certain related embodiments, it is contemplated to provide a dentifrice that is particularly suitable for use with the inventive power toothbrush described herein. For example, it is herein contemplated that such a dentifrice will facilitate the creation of a desirable bubble population that may be acted upon by the ultrasonic transducer 22 and acoustic waveguide 24 disclosed herein.

The natural bubble population within a dental fluid can be assayed by the tendency of that fluid to absorb ultrasonic energy that is transmitted through it. The higher the absorption, the more bubbles that are present at the relevant size (given heuristically by the resonance formula, developed originally for bubbles in pure water at 37 degrees Celsius, although applicable as an approximation for more general conditions $F_0 R_0 = 3.26$, where the frequency $F_0$ is given in MHz and the radius $R_0$ of the bubble is given in microns), although many bubbles off-resonance would also create desired plaque and stain removal effects.

Typically, for example, dentifrices according to the present invention facilitate the formation of bubbles within the dental fluid having a diameter of between about 1 µm and about 150 µm that resonate when ultrasound is applied in the 20 kHz to 3 MHz frequency range. More typically, dentifrices according to the present invention facilitate the formation of bubbles within the dental fluid having a diameter of between about 1 µm and about 100 µm that resonate when ultrasound is applied in the 30 kHz to 3 MHz frequency range. Still more typically, dentifrices according to the present invention facilitate the formation of bubbles within the dental fluid having a diameter of between about 5 µm and about 30 µm that resonate when ultrasound is applied in the 100 kHz to 600 kHz frequency range. In an exemplary dentifrice presented herein, bubbles are formed in the dental fluid that have a diameter of between about 12 µm and about 26 µm that resonate when ultrasound is applied to those bubbles with an ultrasound transducer operating in the 250 kHz to 500 kHz range.

Dentifrices suitable for use with the toothbrushes disclosed herein comprise a surfactant that produces surface tension values that facilitate production and stabilization of bubbles in a suitable size range for stimulation by the ultrasonic transducer in combination with an acoustic waveguide. Typically, surfactants employed in the dentifrices disclosed herein produce surface tensions in the range of about 0.1 Pa to about 500 Pa, more typically in the range of about 0.2 Pa to 250 Pa, and still more typically in the range of about 0.5 Pa to about 50 Pa.

The following examples are provided to exemplify, but not to limit, the presently disclosed invention.

EXAMPLES

Example 1

Design and Construction of a Combined Sonic and Ultrasonic Toothbrush

Prototype power toothbrushes were generated by replacing internal bristle tufts of commercially available power toothbrushes with an ultrasonic transducer and acoustic waveguide. Ultrasonic transducers employed in these prototype toothbrushes had significant power output within the frequency range of about 150 to about 510 kHz that was sufficient to stimulate the formation of an acoustically significant bubble population susceptible to resonant stimulation by energy emitted by the ultrasonic transducer. A polymer waveguide was molded onto the toothbrush head in operable proximity to the ultrasonic transducer and positioned such that ultrasonic waves generated by the ultrasonic transducer were propagated and focused.

Example 2

Ultrasonic Imaging and Plaque Removal by an Exemplary Ultrasonic Power Toothbrush This example discloses ultrasound imaging and plaque removal data collected for one of the prototype power toothbrushes described in Example 1.

Figures 5A, 5B:
FIGS. 5A-5D are ultrasound images of fluid flow generated by an ultrasonic toothbrush with and without a wave guide.
Figures 5C, 5D:

In order to demonstrate the improved performance of a power toothbrush employing an ultrasonic transducer in combination with an acoustic waveguide, Doppler, and B-mode data were collected for a prototype ultrasonic toothbrush with and without incorporating an acoustic waveguide. FIG. 5A presents an ultrasound image of an ultrasonic toothbrush without an acoustic waveguide. Doppler data show fluid flow (within box) and B-mode data highlight acoustic backscatter (outside of box) at the bristle tips (BT) and bristle plate (BP) at bottom of bristles. FIG. 5B presents the same ultrasonic toothbrush with moving bristles powered by a sonic component. These data reveal that fluid flow (FF) beyond the bristle tips is not detectable even though the bristles are moving (MB). FIG. 5C presents an ultrasound B-mode image of a prototype ultrasonic toothbrush in combination with an acoustic waveguide. The sonic component drives the vibration of the acoustic waveguide and generates a jet of bubbly fluid moving away from the brush. FIG. 5D presents Doppler and B-mode ultrasound image data of the same toothbrush showing significant fluid flow (FF) and bubbles (B) beyond the bristles.

A prototype ultrasonic power toothbrush was tested for plaque removal in a plaque coated (*Streptococcus mutans*) artificial tooth model system. Plaque was detected by staining a set of artificial teeth before application of fluid flow generated by an acoustic waveguide, without ultrasound, positioned several millimeters beyond the toothbrush head bristle tips. Discrete plaque colonies were reduced or removed after application of fluid flow generated by the ultrasonic transducer in combination with the acoustic waveguide.

An artificial tooth model for tooth areas outside the reach of a toothbrush head bristle tip was also tested. Plaque was dyed pink before application of ultrasonic energy from several millimeters beyond the bristle tips. Discrete plaque colonies were reduced or removed after application of ultrasound. Background films of plaque were also reduced, leaving residual pink due primarily to dye that has leached into the teeth. Plaque removal in the same model system was also tested after application of fluid flow generated by an acoustic waveguide and after application of ultrasonic energy from several millimeters beyond the bristles. Discrete plaque colonies were reduced or removed after treatment. Background films of plaque were also reduced, leaving residual pink due primarily to dye that has leached into the teeth. Superior results were achieved while simultaneously using microscopic fluid flow from the acoustic waveguide and ultrasound.

Example 3

Measurement of Physical Parameters of an Exemplary Ultrasonic Power Toothbrush Employing an Acoustic Waveguide This example discloses measurements of physical parameters of an exemplary ultrasonic power toothbrush of the present invention.

Figure 6:
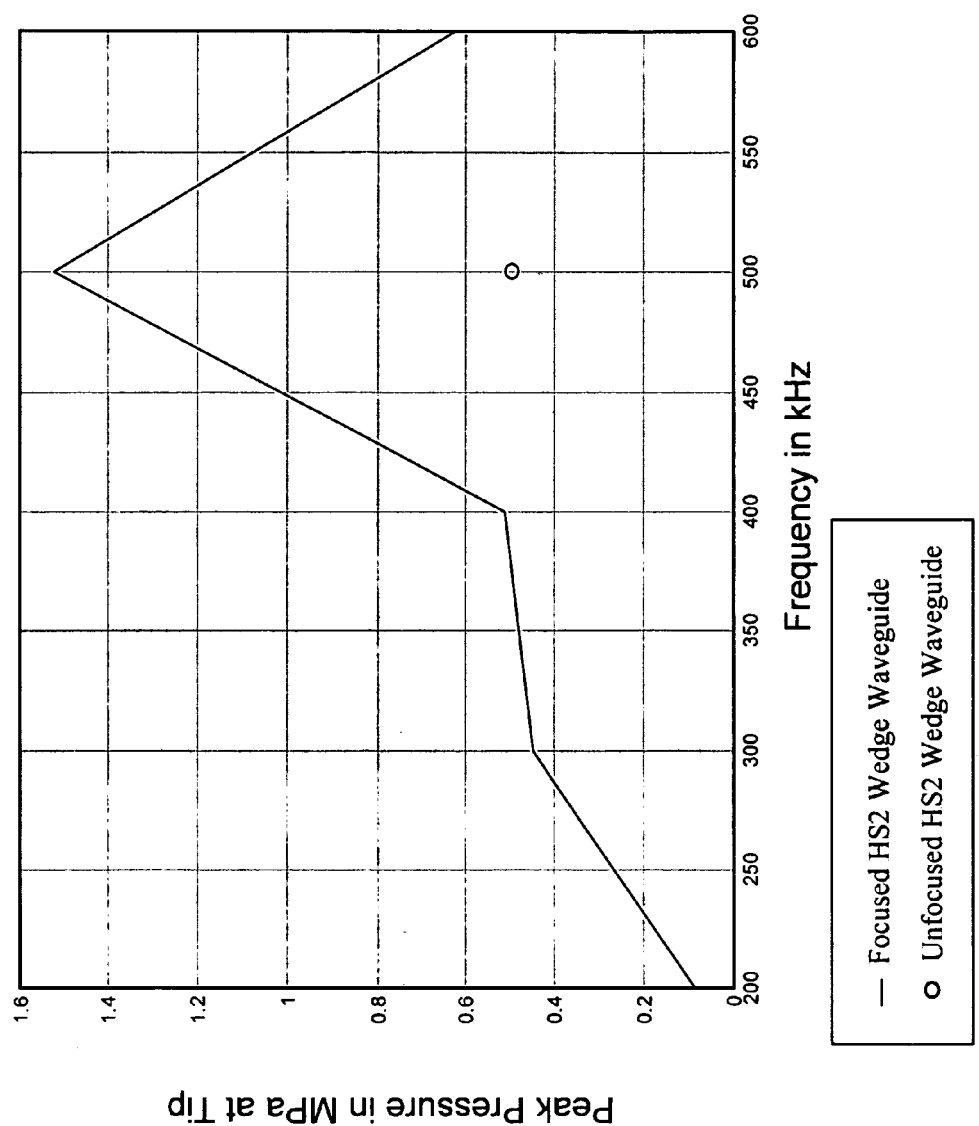
FIG. 6 is a plot comparing the measured acoustic pressure levels at the tip of a flat versus a focused lens acoustic waveguide.

In order to compare the effectiveness of various acoustic waveguide geometries, the transmitting pressures for a flat, unfocused elastomeric/silicone polymer wedge waveguide was compared to the transmitting pressures for a focused elastomeric/silicone polymer wedge waveguide. The plot of acoustic pressure levels at the tip of each acoustic waveguide presented in FIG. 6 demonstrates an approximately three-fold increase in transmitting pressure for a focused waveguide (~1.5 MPa tip pressure) versus an unfocused waveguide (~0.5 MPa tip pressure).

Figure 7:
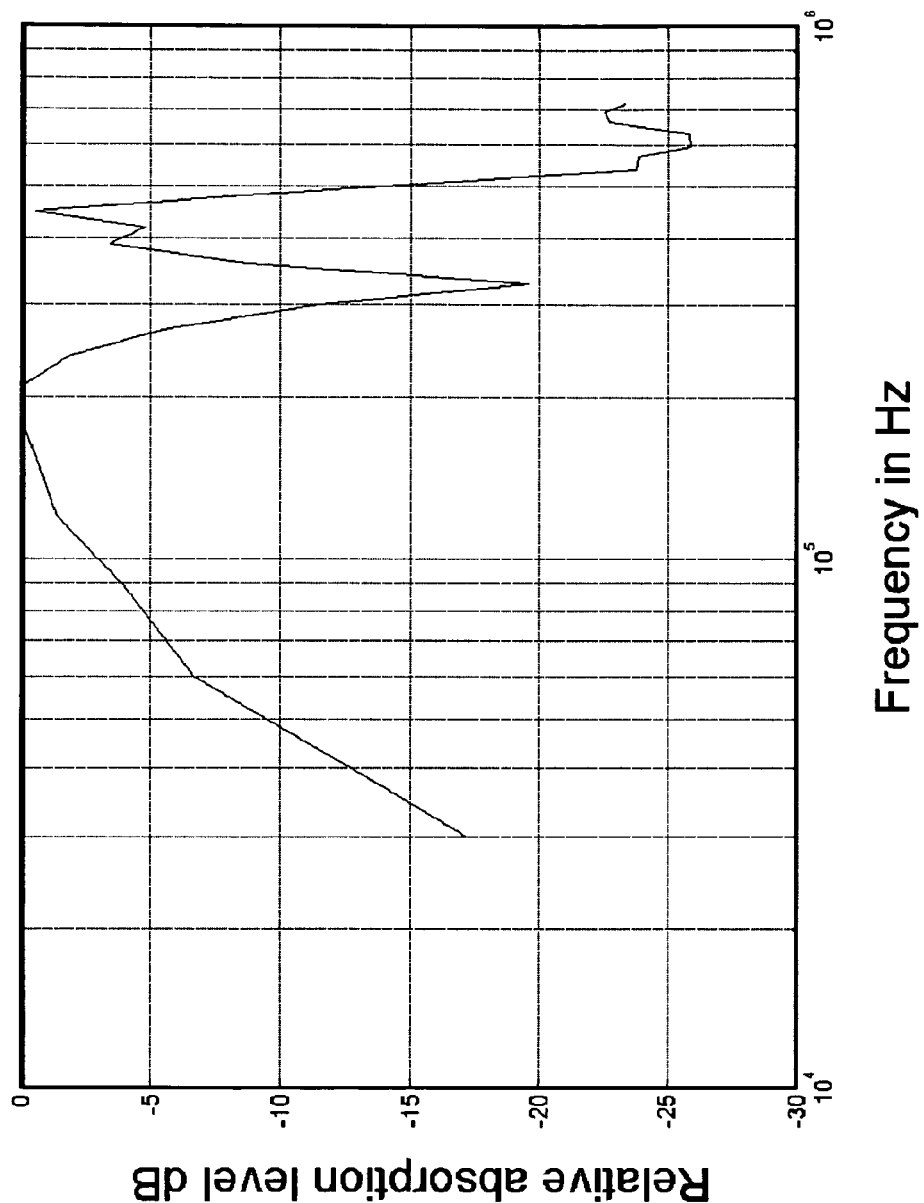
FIG. 7 is a plot showing the absorption of ultrasound waves transmitted through a dental fluid/bubble emulsion versus frequency.

The absorption of ultrasound transmitted through a model dental fluid/bubble emulsion was measured as a function of ultrasonic frequency in the 30 to 700 kHz frequency range. Ultrasonic transducers were positioned on opposite sides, approximately 0.3 to 1 cm apart, on opposite sides of a Petri dish containing simulated dental fluid (i.e., an emulsification of dentifrice and water) and the intensity of sound transmitted through the fluid was measured and normalized by the intensity of sound transmitted into the fluid. Results of an exemplary test are presented in FIG. 7, which reveals a peak in attenuation due to absorption of sound at approximately 200 kHz and a spurious dip in the curve at approximately 350 kHz, owing to resonance between the length of the ultrasound wave and the depth of the fluid. These data demonstrated the presence of a significant bubble population available for acoustic stimulation at frequencies between 100-500 kHz.

Example 4

Plaque Removal by an Exemplary Ultrasonic Power Toothbrush

This example discloses plaque removal with the bubbly jet generated by the sonic vibration of an acoustic waveguide in combination with ultrasound stimulation of the bubbles within the jet.

A *Streptococcus mutans* model for dental plaque was employed to assess plaque removal by an exemplary ultrasonic toothbrush of the present invention. *S. mutans* (human-derived plaque) was allowed to grow on frosted glass slides, then exposed to a prototype toothbrush operated at the surface of a water bath and held a few millimeters away from, in a perpendicular fashion, the surface of the slide. A variety of ultrasound protocols were used, including waveguide only (WG) and waveguide plus ultrasound (WG/US). The slides were stained with a plaque-specific dye to indicate intact plaque (pink) and plaque-free regions (white).

In an exemplary assay, the surface of an *S. mutans*-coated slide was placed 4 mm from the longest bristles of a prototype toothbrush. The ultrasound carrier frequency was 250 kHz, with a PRF of 1000 Hz and with 24 cycles per burst; the Mechanical Index was 0.75. With only the bubbly fluid jet produced by the acoustic waveguide, there was a subtle reduction in the thickness of the plaque, while in concert with ultrasound, significant plaque was removed. For comparison, a commercially available power toothbrush was held at the same distance from plaque grown on the frosted glass slide. That control toothbrush did not remove meaningful plaque.

A second assay system used hydroxyapatite (HA) disks incubated for 48 hours prior to the experiment with *S. Mutans*. The ultrasound protocol consisted of a 250 kHz run at 625 Hz PRF, 40 cycles/sec, 3 second exposure, and a Mechanical Index of 0.9 measured at 6 mm from the tip of the acoustic waveguide.

The action of the acoustic waveguide alone removed some plaque; however, in combination with ultrasound, there was significantly improved plaque removal. By comparison, a commercially available power toothbrush did not remove any plaque, while ultrasound alone removed only a few spots of plaque, in a small region of the disk.

In a third experimental system, an ultrasound protocol was followed that consisted of a 510 kHz run at 1,252 Hz PRF, with 2 cycles/sec, exposed for 3 seconds, with a Mechanical Index of 0.51 measured at 6 mm from the tip of the waveguide. Consistent with the assays described above, the action of the acoustic waveguide alone removed some plaque; but, in combination with ultrasound, there was significantly improved plaque removal. By comparison, a commercially available power toothbrush, held 1-2 mm away from the front of the teeth, removed only some plaque, while ultrasound alone only removed a few spots of plaque in a small region of the disk. Thus, the bubbly fluid jet generated by the sonically vibrating acoustic waveguide was sufficient to achieve more rapid plaque removal beyond the reach of the bristles by a factor of at least two-fold greater than the commercial power toothbrush.

Plaque removal was observed across a wide range of acoustic protocols. Optimal plaque removal was achieved when the PRF was a multiple, greater than one, of the sonic frequency. Without wishing to be bound to any specific theory of operation, it is believed that this protocol resulted in optimal plaque removal because it allowed multiple pulses of ultrasound to interact with the bubbly jet and the plaque as the flexible tip of the acoustic waveguide was being oscillated back and forth across the face of the HA disk, relevant portion of the glass slides, and/or the teeth. It is further believed that this accounts, at least in part, to the synergistic effect observed with the combined action of a bubbly fluid jet and ultrasound.

In order to demonstrate this synergistic effect, the action of ultrasound alone on a tooth/model of plaque removal was assessed both with and without motion of the acoustic waveguide. An ultrasound protocol was chosen that, by itself, did not yield meaningful plaque removal (with or without the production of a bubbly jet), but did so after introduction of dental fluid containing artificial bubbles (Optison™). The results of this study also demonstrated that ultrasound alone was not responsible for plaque removal; but, rather, it was the ultrasound stimulation of the artificial bubbles that, in combination, yielded substantial plaque removal.

Additional studies performed in an artificial tooth dental plaque model for tooth areas beyond the reach of the toothbrush's bristles demonstrated that a sonically vibrating acoustic waveguide simultaneously emitting ultrasound at 450 kHz in the presence of artificial bubbles removed plaque from a distance of 2-3 mm after only 5 seconds of application, although that plaque removal pattern actually appeared within a fraction of a second of ultrasound onset. This plaque removal occurred over a larger area than with ultrasound alone and occurred in an appreciably shorter length of time than that created by the bubbly fluid jet alone. Therefore, the ultrasound and sonically generated bubbly fluid flow acted together in a synergistic fashion to rapidly and effectively remove plaque over a large area, beyond the reach of the bristles.

Because a bubble's volume oscillates and associated stresses act on a time scale governed by the ultrasound frequency, the frequencies (on the order of 100s of kHz), plaque removal can, in principle, occur on time scales on the order of 0.00001 seconds (i.e., approximately 10 microseconds). Therefore, ultrasound toothbrushes of the present invention are capable of substantial plaque removal at times that are approximately 100- to 1000-fold shorter than the time required for plaque removal by existing power toothbrushes.

Example 5

Absence of Cell Lysis by an Exemplary Ultrasonic Power Toothbrush

This example discloses that ultrasonic power toothbrushes of the present invention induces ultrasonic cavitation whose mechanical effects were insufficient to induce cell lysis, yet were able to remove plaque. These findings support the safety of ultrasonic power toothbrushes provided herein.

Figure 8:
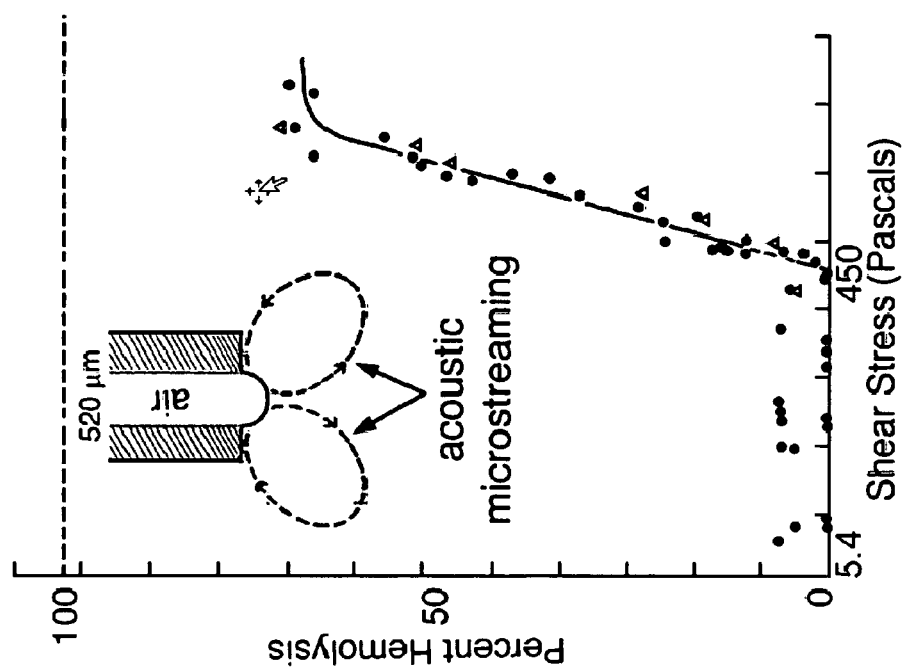
FIG. 8 is a plot showing the percent of suspended red blood cells destroyed by shear stress induced by acoustic microstreaming associated with a stably oscillating bubble. The inset depicts a thin, hollow wire with air in its center, placed within a vial of suspended red blood cells.

A red blood cell model system was utilized (FIG. 8) to test cell lysis caused by shear stresses induced by acoustic microstreaming associated with stable oscillating bubbles by Rooney, Science 169:869-871 (1970), who demonstrated that a single bubble, placed within a vial of dilute red blood cells, could be stimulated by ultrasound to produce "microstreaming" such that with sufficient acoustic power, those blood cells could be disrupted. In particular, a thin, hollow wire with air in its center was placed in a vial of suspended red blood cells. Sufficient air was extruded from the wire to form a hemisphere of gas (the microbubble) within the suspension. Ultrasonic waves at a frequency of about 25 kHz were applied to the container to stimulate oscillation of the bubbles and sufficient to generate acoustic microstreaming. Under these conditions, about 70% of the red blood cells were destroyed at shear stresses comparable to those determined via independent means. One hundred percent hemolysis was achieved by introduction of a highly osmotic solution. Of particular interest here is the difference in shear stress (greater than 450 Pa) necessary to break up the cells, versus stress necessary to remove fresh plaque in vitro (1-30 Pa). The shear required for detachment of P. aeruginosa biofilms grown at shear stresses of 0.075 and 5.09 Pa were 5.09 Pa and 25.3 Pa, respectively. Stoodley et al., Journal of Industrial Microbiology & Biotechnology 29:361-367 (2002).

Acoustic microstreaming, just one of a variety of physical processes associated with acoustic cavitation (the formation and/or stimulation of bubbles by acoustic energy), can cause disruption of biological systems such as red blood cells, as discussed herein. Of particular interest is that the presence of bubbles can facilitate stresses sufficient to remove plaque, for example, at acoustic intensities far below that necessary to cause desired biological effects, when no bubbles are present. In the present example, Optison™, a microbubble ultrasound (US) contrast agent with a diameter of about one micron, was used to demonstrate this point. This example also shows that it is the ultrasound stimulation of bubbles, not ultrasound cavitation alone, that removes plaque.

As evidence for the safety of ultrasonic toothbrushes of the present invention, the following plaque removal assay system was employed. Cell disruption by an exemplary toothbrush was determined by assaying cell debris in the liquid above plated gingival cells that were exposed to (1) an activated commercial power toothbrush whose bristle tips were placed above the cells, (2) a bubbly fluid jet caused by the sonic component of the prototype toothbrush held above the cells, and (3) the combination of bubbly fluid jet and ultrasound (sonic plus ultrasound) from the prototype toothbrush, held above the cells. These results were compared to the results achieved with a commercial power toothbrush whose bristle tips were placed directly on the cells.

Following treatment, supernatants were evaluated for lysed cells by a nonradioactive lactate dehydrogenase (LDH) assay (Cytotox 96; Promega, Madison, Wis.) according to the manufacturer's instructions. This assay system is a calorimetric alternative to $^{51}$Cr release cytotoxicity assays and has been used to measure cell lysis by chemical and physical means. Singer et al., J. Neurosci. 19:2455-2463 (1999). The assay quantitatively measures LDH, a stable cytosolic enzyme that is released upon cell lysis in much the same way as $^{51}$Cr is released in radioactive assays. Released LDH in culture supernatants is measured with a 30-minute coupled enzymatic assay, which results in the conversion of a tetrazolium salt (INT) into a red formazan product. The amount of color formed is proportional to the number of lysed cells.

Visible wavelength absorbance data were collected using a standard 96 well plate reader. Methods for determination of LDH utilizing tetrazolium salts in conjunction with diaphorase or alternate electron acceptors are well known in the art. Variations on this technology have been reported for measuring natural cytotoxicity and have been demonstrated to be identical (within experimental error) to values determined in parallel $^{51}$Cr release assays.

Cells remaining in plates following treatment were photographed, lysed, and quantified using the LDH assay as described above. Cell lysis induced by the beyond the bristle effects of a sonic toothbrush was compared to cell lysis induced by a prototype combined sonic/ultrasonic toothbrush of the present invention.

Figure 10:
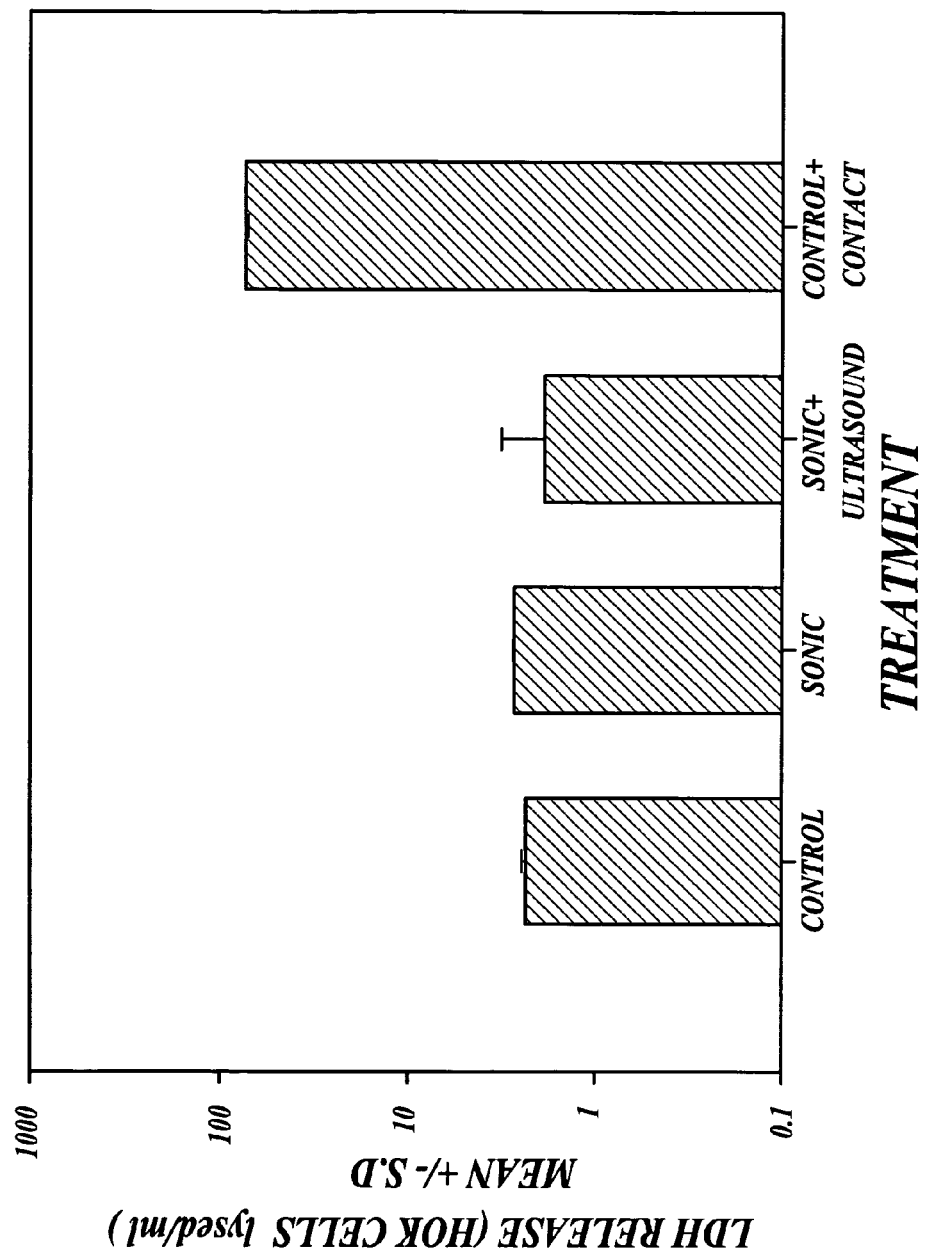
FIG. 10 is a bar graph of data demonstrating the safety of a toothbrush according to the present invention.

Results of an exemplary assay are presented in FIG. 10, which demonstrate that the cleaning action of a bubbly fluid jet generated by an acoustic waveguide mounted on a toothbrush, in combination with ultrasound propagated through the acoustic waveguide, safely removed plaque. The "control" result was a measure of cell lysis caused by the fluid action generated beyond the reach of the bristles of a commercial power toothbrush; the "sonic" result was a measure of such cell lysis by an exemplary toothbrush without ultrasound; the "sonic+ultrasonic" result was a measure of such cell lysis by an exemplary toothbrush with both a sonic component and ultrasound; and the "control+contact" result was a measure of cell lysis by a commercial power toothbrush whose bristles were placed in direct contact with the cell surface. There were no differences detected between the commercial toothbrush and the prototypical toothbrush when their bristles did not touch the cells. In contrast, there was substantial cell lysis generated by the direct contact of the toothbrush bristles of a commercial power toothbrush upon the cells.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A toothbrush comprising:
 a toothbrush head having an outwardly extending acoustic waveguide;
 an ultrasonic transducer operably connected to transmit ultrasonic waves through the acoustic waveguide; and
 a handle operatively connected to the toothbrush head, the handle having a component that vibrates the toothbrush head during operation.

2. The toothbrush of claim 1, wherein the component is a sonic component that vibrates the toothbrush head at a frequency between about 20 Hz and 20 kHz.

3. The toothbrush of claim 2, wherein the toothbrush head further comprises a plurality of outwardly extending bristles.

4. The toothbrush of claim 1, wherein the toothbrush head is removably connected to the handle.

5. The toothbrush of claim 1, wherein the acoustic waveguide is formed from a polymer.

6. The toothbrush of claim 5, wherein the polymer is selected from a room temperature vulcanizing silicone, a liquid injected molded silicone, and a thermal plastic elastomer.

7. The toothbrush of claim 1, wherein the acoustic waveguide is formed from a dielectric material.

8. The toothbrush of claim 1, wherein the acoustic waveguide is formed from a material having a hardness between about 5 and about 200 Shore A.

9. The toothbrush of claim 8, wherein the acoustic waveguide is formed from a material having a hardness between about 20 and about 80 Shore A.

10. The toothbrush of claim 1, wherein the acoustic waveguide is generally wedge-shaped.

11. The toothbrush of claim 1, additionally comprising an ultrasonic module drive circuit driving the ultrasonic transducer at a frequency within the range of about 20 kHz to about 3 MHz during operation.

12. The toothbrush of claim 11, wherein the ultrasonic module drive circuit drives the ultrasonic transducer at a frequency within the range of about 100 kHz to about 750 kHz during operation.

13. The toothbrush of claim 1, additionally comprising an ultrasonic module drive circuit driving the ultrasonic transducer for a duty cycle between about 1% and about 10% during operation.

14. The toothbrush of claim 1, additionally comprising an ultrasonic module drive circuit driving the ultrasonic transducer for a duty cycle of at least about 10% during operation.

15. The toothbrush of claim 1, wherein the toothbrush produces a mechanical index in the range of about 0.01 to about 1.9 during operation.

16. The toothbrush of claim 1, wherein the ultrasonic transducer generates bursts of ultrasound comprising between about 1 and about 5000 individual ultrasound waves.

17. The toothbrush of claim 1, wherein the pulse repetition frequency of the ultrasonic transducer ranges between about 1 Hz and about 10,000 Hz during operation.

18. The toothbrush of claim 1, wherein the toothbrush head is fixedly attached to the handle.

19. The toothbrush of claim 1, wherein the acoustic waveguide is a flexible mechanical protrusion that is adapted to extend into the denial fluid during operation.

20. The toothbrush of claim 1, wherein the ultrasonic transducer is in direct contact with the acoustic waveguide.

21. The toothbrush of claim 1, additionally comprising an impedance matching layer positioned between the ultrasonic transducer and the acoustic waveguide that improves the efficiency of transmitting ultrasonic waves into the acoustic waveguide.

22. The toothbrush of claim 1, wherein the acoustic waveguide comprises a conical portion.

23. The toothbrush of claim 1, wherein tile acoustic waveguide comprises a pyramid-shaped portion.

24. The toothbrush of claim 1, wherein tile acoustic waveguide comprises a bullet-shaped body.

25. The toothbrush of claim 1, wherein the acoustic waveguide has a curved distal surface.

26. The toothbrush of claim 1, wherein the acoustic waveguide is rectangular.

27. The toothbrush of claim 1, wherein the acoustic waveguide has tapered sidewalls.

28. The toothbrush of claim 1, wherein the acoustic waveguide is capable of acoustic incoherent focusing of ultrasonic waves.

29. The toothbrush of claim 1, wherein the toothbrush generates fluid flows of at least 2 cm/sec at a distance of between about 1 mm and 10 mm beyond the acoustic waveguide during operation.

30. The toothbrush of claim 1, additionally comprising an element behind and extending around each side of the ultrasonic transducer to at least partially reflect the ultrasonic waves through the acoustic waveguide.

31. The toothbrush of claim 1 wherein the ultrasonic transducer and acoustic waveguide are adapted to generate cavitation within a user's dental fluid during operation.

32. The toothbrush of claim 1 that, during operation, induces cavitation and microstreaming within the dental fluid.

33. The toothbrush of claim 1 that, during operation, produces shear forces associated with cavitating microbubbles within dental fluid that are distributed along surfaces of gums and teeth and in interproximal and subgingival spaces.

34. A toothbrush comprising:
a toothbrush head having an outwardly extending acoustic waveguide; and
a handle operatively connected to the toothbrush head, the handle having a component that vibrates the toothbrush head;
wherein the acoustic waveguide comprises a plurality of layers, at least two of the layers having differing material properties.

35. The toothbrush of claim 34, wherein the acoustic waveguide includes a graphite layer and a polymer layer, and wherein the polymer layer is molded around the graphite layer.

36. The toothbrush of claim 34, wherein the acoustic waveguide includes a first layer having a Shore A hardness of at least 80, a second layer in contact with the first layer, the second layer having a Shore A hardness of between about 20 and 80, and a third layer in contact with the second layer, the third layer having a Shore A hardness of not more than 20.

37. A toothbrush comprising:
a toothbrush head having an outwardly extending acoustic waveguide;
an ultrasonic transducer operably connected to the acoustic waveguide such that the ultrasonic transducer propagates ultrasonic waves having a frequency greater than about 20 kHz through the acoustic waveguide; and
a handle operatively connected to the toothbrush head.

38. The toothbrush of claim 37, wherein the toothbrush head further comprises a plurality of outwardly extending bristles.

39. The toothbrush of claim 37, wherein the toothbrush head is removably connected to the handle.

40. The toothbrush of claim 37, wherein the acoustic waveguide is formed from a polymer.

41. The toothbrush of claim 40 wherein the polymer is selected from a room temperature vulcanizing silicone, a liquid injected molded silicone, and a thermal plastic elastomer.

42. The toothbrush of claim 37, wherein the acoustic waveguide is formed from a dielectric material.

43. The toothbrush of claim 37, wherein the acoustic waveguide is formed from a material having a hardness between about 5 and about 200 Shore A.

44. The toothbrush of claim 37, wherein the acoustic waveguide is formed from a material having a hardness between about 20 and about 80 Shore A.

45. The toothbrush of claim 37, wherein the acoustic waveguide comprises a plurality of layers, at least two of the layers having differing material properties.

46. The toothbrush of claim 45, wherein the acoustic waveguide includes a graphite layer and a polymer layer, and wherein the polymer layer is molded around the graphite layer.

47. The toothbrush of claim 45 wherein the acoustic waveguide includes a first layer having a Shore A hardness of at least 80, a second layer in contact with the first layer, the second layer having a Shore A hardness of between about 20 and 80, and a third layer in contact with the second layer, the third layer having a Shore A hardness of not more than 20.

48. The toothbrush of claim 37, wherein the acoustic waveguide is wedge-shaped.

49. The toothbrush of claim 37, wherein the acoustic waveguide is shaped to coherently focus the ultrasonic waves.

50. The toothbrush of claim 37, wherein the acoustic waveguide is shaped to compress the ultrasonic waves.

51. The toothbrush of claim 37, wherein the ultrasonic transducer is selected from the group consisting of a piezoelectric transducer, a magnetostrictive transducer, a micromachined capacitive ultrasonic transducer, and an electrostatic polymer foam transducer.

52. The toothbrush of claim 51, wherein the ultrasonic transducer is a piezoelectric transducer comprising a material selected from the group consisting of lead zirconate titanate, polyvinylidene fluoride, lithium niobate, quartz, and barium titanate.

53. The toothbrush of claim 37, further comprising an impedance matching layer in operable contact with the ultrasonic transducer.

54. The toothbrush of claim 37, further comprising a sonic component that vibrates the toothbrush head at a frequency between about 20 Hz and 20 kHz.

55. The toothbrush of claim 37, additionally comprising an ultrasonic module drive circuit driving the ultrasonic transducer at a frequency within the range of about 20 kHz to about 3 MHz during operation.

56. The toothbrush of claim 55, wherein the ultrasonic module drive circuit drives the ultrasonic transducer at a frequency within the range of about 100 kHz to about 750 kHz during operation.

57. The toothbrush of claim 37, additionally comprising an ultrasonic module drive circuit driving the ultrasonic transducer for a duty cycle between about 1% and about 10% during operation.

58. The toothbrush of claim 37, additionally comprising an ultrasonic module drive circuit driving the ultrasonic transducer for a duty cycle of at least about 10% during operation.

59. The toothbrush of claim 37 wherein the toothbrush produces a mechanical index in the range of about 0.01 to about 1.9 during operation.

60. The toothbrush of claim 37 wherein the number of individual ultrasonic waves within a packet is between about 1 and about 5,000 during operation of the ultrasonic transducer.

61. The toothbrush of claim 37, wherein the pulse repetition frequency of the ultrasonic transducer ranges between about 1 Hz and about 10,000 Hz during operation.

62. The toothbrush of claim 37 wherein the toothbrush head is fixedly attached to the handle.

63. The toothbrush of claim 37 wherein the acoustic waveguide is a flexible mechanical protrusion that extends into the dental fluid during operation.

64. The toothbrush of claim 37 wherein the ultrasonic transducer is in direct contact with the acoustic waveguide.

65. The toothbrush of claim 37 additionally comprising an impedance matching layer positioned between the ultrasonic transducer and the acoustic waveguide that improves the efficiency of transmitting ultrasonic waves into the acoustic waveguide.

66. The toothbrush of claim 37 wherein the acoustic waveguide comprises a conical portion.

67. The toothbrush of claim 37 wherein the acoustic waveguide comprises a pyramid-shaped portion.

68. The toothbrush of claim 37 wherein the acoustic waveguide comprises a bullet-shaped body.

69. The toothbrush of claim 37 wherein the acoustic waveguide has a curved distal surface.

70. The toothbrush of claim 37 wherein the acoustic waveguide is rectangular.

71. The toothbrush of claim 37 wherein the acoustic waveguide has tapered sidewalls.

72. The toothbrush of claim 37 wherein the acoustic waveguide is capable of acoustic incoherent focusing of ultrasonic waves.

73. The toothbrush of claim 37 wherein the toothbrush generates fluid flows of at least 2 cm/sec at a distance of between about 1 mm and 10 mm beyond the acoustic waveguide during operation.

74. The toothbrush of claim 37, additionally comprising an clement behind and extending around each side of the ultrasonic transducer to at least partially reflect the ultrasonic waves through the acoustic waveguide.

75. The toothbrush of claim 37 wherein the ultrasonic transducer and acoustic waveguide are adapted to generate cavitation within a user's dental fluid (luring operation.

76. The toothbrush of claim 37 wherein the ultrasonic transducer and acoustic waveguide are adapted to generate microstreaming of microbubbles within a user's dental fluid during operation.

77. A removable toothbrush head having a base, a plurality of bristles extending from the base, an acoustic waveguide extending from the base, and an ultrasonic transducer in operable proximity to the acoustic waveguide such that ultrasonic waves are propagated into and through the acoustic waveguide from the ultrasonic transducer during operation.

78. The removable toothbrush head of claim 77 wherein the acoustic waveguide is formed from a polymer.

79. The removable toothbrush head of claim 77 wherein the polymer is selected from a room temperature vulcanizing silicone, a liquid injected molded silicone, and a thermal plastic elastomer.

80. The removable toothbrush head of claim 77, wherein the acoustic waveguide is formed from a dielectric material.

81. The removable toothbrush head of claim 77, wherein the acoustic waveguide is formed from a material having a hardness between about 5 and about 200 Shore A.

82. The removable toothbrush head of claim 81, wherein the acoustic waveguide is formed from a material having a hardness between about 20 and about 80 Shore A.

83. The removable toothbrush head of claim 77, wherein the acoustic waveguide is generally wedge-shaped.

84. The removable toothbrush head of claim 77, wherein the acoustic waveguide is a flexible mechanical protrusion that extends into dental fluid during operation.

85. The removable toothbrush head of claim 77, wherein the ultrasonic transducer is selected from the group consisting of a piezoelectric transducer, a magnetostrictive transducer, a micromachined capacitive ultrasonic transducer, and an electrostatic polymer foam transducer.

86. The removable toothbrush head of claim 85, wherein the ultrasonic transducer is a piezoelectric transducer comprising a material selected from the group consisting of lead zirconate titanate, polyvinylidene fluoride, lithium niobate, quartz, and barium titanate.

87. A removable toothbrush head, having a base, a plurality of bristles extending from the base, and an acoustic waveguide extending from the base, wherein the acoustic waveguide comprises a plurality of layers, at least two of the layers having differing material properties.

88. The removable toothbrush head of claim 87, wherein the acoustic waveguide includes a graphite layer and a polymer layer, and wherein the polymer layer is molded around the graphite layer.

89. The removable toothbrush head of claim 87, wherein the acoustic waveguide includes a first layer having a Shore A hardness of at least 80, a second layer in contact with the first layer, the second layer having a Shore A hardness of between about 20 and 80, arid a third layer in contact with the second layer, the third layer having a Shore A hardness of not more than 20.

90. A toothbrush comprising:
a toothbrush head having an outwardly extending acoustic waveguide formed as a flexible mechanical protrusion;
an ultrasonic transducer mechanically coupled to the acoustic waveguide to propagate ultrasonic sound waves into and through the acoustic waveguide during operation; and
a handle operatively connected to the toothbrush head.

91. The toothbrush of claim 90, additionally comprising a sonic component that vibrates the toothbrush head at a frequency of between about 20 Hz and 20 kHz during operation.

92. The toothbrush of claim 90, additionally comprising an ultrasonic module drive circuit driving the ultrasonic transducer at a frequency within the range of about 20 kHz to about 3 MHz during operation.

93. The toothbrush of claim 92, wherein the ultrasonic module drive circuit drives the ultrasonic transducer at a frequency within the range of about 100 kHz to about 750 kHz during operation.

94. The toothbrush of claim 90, wherein the toothbrush produces a mechanical index in the range of about 0.01 to about 1.9 during operation.

95. The toothbrush of claim 90, wherein the toothbrush head is fixedly attached to the handle.

96. The toothbrush of claim 90, wherein the acoustic waveguide has a curved distal surface.

97. The toothbrush claim 90, wherein the acoustic waveguide is rectangular.

98. The toothbrush of claim 90, wherein the acoustic waveguide has tapered sidewalls.

99. The toothbrush of claim 90, wherein the toothbrush generates fluid flows of at least 2 cm/sec at a distance of between about 1 mm and 10 mm beyond time acoustic waveguide during operation.

* * * * *

UNITED STATES PATENT AND TRADEMARK OFFICE
CERTIFICATE OF CORRECTION

PATENT NO. : 7,296,318 B2
APPLICATION NO. : 10/981735
DATED : November 20, 2007
INVENTOR(S) : P.D. Mourad et al.

It is certified that error appears in the above-identified patent and that said Letters Patent is hereby corrected as shown below:

On the Title Page
Item (56)     Refs. Cited        "Ultrasoound" should read --Ultrasound--
Pg. 2,        (Other Publs.,
              Item 7)

Col. 26       line 23            "denial fluid" should read --dental fluid--
     (Claim 19)

Col. 26       line 34            "tile" should read --the--
     (Claim 23)

Col. 26       line 36            "tile" should read --the--
     (Claim 24)

Col. 29       line 11            "clement" should read --element--
     (Claim 74)

Col. 29       line 16            "(luring" should read --during--
     (Claim 75)

Col. 30       line 46            before "claim 90," insert --of--
     (Claim 97)

Col. 30       line 53            "time" should read --the--
     (Claim 99)

Signed and Sealed this

Third Day of June, 2008

JON W. DUDAS
*Director of the United States Patent and Trademark Office*